US009212176B2

(12) United States Patent
Mullen et al.

(10) Patent No.: US 9,212,176 B2
(45) Date of Patent: *Dec. 15, 2015

(54) POLYKETAL ADDUCTS, METHODS OF MANUFACTURE AND USES THEREOF

(75) Inventors: Brian D. Mullen, Delano, MN (US); Marc D. Scholten, Saint Paul, MN (US); Tara J. Mullen, Delano, MN (US); Cora M. Leibig, Maple Grove, MN (US); Vivek Badarinarayana, Saint Louis Park, MN (US); Matthew J. Tjosaas, Grand Rapids, MI (US)

(73) Assignee: SEGETIS, INC., Golden Valley, MN (US)

(*) Notice: Subject to any disclaimer, the term of this patent is extended or adjusted under 35 U.S.C. 154(b) by 418 days.

This patent is subject to a terminal disclaimer.

(21) Appl. No.: 13/294,690

(22) Filed: Nov. 11, 2011

(65) Prior Publication Data
US 2012/0118201 A1 May 17, 2012

Related U.S. Application Data

(60) Provisional application No. 61/508,974, filed on Jul. 18, 2011, provisional application No. 61/412,573, filed on Nov. 11, 2010.

(51) Int. Cl.
*C07D 407/12* (2006.01)
*C08K 5/1565* (2006.01)
*C08L 79/08* (2006.01)
*C08L 77/00* (2006.01)
*C08L 59/02* (2006.01)

(52) U.S. Cl.
CPC ............ *C07D 407/12* (2013.01); *C08K 5/1565* (2013.01); *C08L 59/02* (2013.01); *C08L 77/00* (2013.01); *C08L 79/08* (2013.01)

(58) Field of Classification Search
CPC .... C07D 407/12; C08K 5/1565; C08L 59/02; C08L 77/00; C08L 79/08; C08L 27/06
USPC .................. 106/203.3; 549/430, 448; 524/108
See application file for complete search history.

(56) References Cited

U.S. PATENT DOCUMENTS

| | | |
|---|---|---|
| 2,004,115 A | 6/1935 | Izard et al. |
| 2,008,720 A | 7/1935 | Lawson et al. |
| 2,260,261 A | 1/1940 | Morey |
| 2,556,135 A | 6/1951 | Croxall et al. |
| 2,838,467 A | 6/1958 | Dobay |
| 2,985,536 A | 5/1961 | Stein et al. |
| 3,041,313 A | 6/1962 | Lavin et al. |
| 3,201,420 A | 8/1965 | Fuzesi et al. |
| 3,963,800 A | 6/1976 | Gipp et al. |
| 4,085,081 A | 4/1978 | Heckles et al. |
| 4,792,411 A | 12/1988 | Walsh |
| 5,095,098 A | 3/1992 | McLain et al. |
| 5,202,413 A | 4/1993 | Spinu et al. |
| 5,552,513 A | 9/1996 | Bhatia |
| 5,565,545 A | 10/1996 | Kriesche et al. |
| 5,741,882 A | 4/1998 | Fujii et al. |
| 5,917,059 A | 6/1999 | Bruchmann et al. |
| 5,998,092 A | 12/1999 | McCulloch et al. |
| 6,143,908 A | 11/2000 | Hinoue et al. |
| 6,528,025 B1 | 3/2003 | Boesch et al. |
| 6,806,392 B2 | 10/2004 | Boesch et al. |
| 2003/0167681 A1 | 9/2003 | Delgado Puche |
| 2003/0204042 A1 | 10/2003 | Moethrath et al. |
| 2004/0024260 A1 | 2/2004 | Winkler et al. |
| 2006/0069230 A1 | 3/2006 | Papisov |
| 2007/0155820 A1 | 7/2007 | Gant et al. |
| 2008/0242721 A1 | 10/2008 | Selifonov |
| 2010/0048940 A1 | 2/2010 | Tulchinsky et al. |
| 2010/0216915 A1 | 8/2010 | Bloom |
| 2011/0021658 A1 | 1/2011 | Selifonov et al. |
| 2012/0035376 A1 | 2/2012 | Mullen et al. |
| 2013/0053564 A1 | 2/2013 | Selifonov et al. |
| 2013/0310288 A1 | 11/2013 | Mullen et al. |

FOREIGN PATENT DOCUMENTS

| | | |
|---|---|---|
| DE | 1031512 | 6/1958 |
| FR | 1445013 | 7/1966 |
| JP | 28004327 | 9/1953 |
| JP | 2002348451 A | 12/2002 |
| WO | 2005097723 A2 | 10/2005 |
| WO | 2007062118 A2 | 5/2007 |
| WO | WO2007/094922 A2 | 8/2007 |

(Continued)

OTHER PUBLICATIONS

Smith, M. ,March's Advanced Organic Chemistry: Reactions, Mechanisms, and Structure, 2007, Wiley Interscience, Chapter 16, p. 1251-1274.*
Wuts, P.G.M., Greene's Protective Groups in Organic Synthesis, 2006, Fourth Edition, John Wiley and Sons, Chapter 5. p. 533-646.*
International Preliminary Report on Patentability for PCT/US2011/060450 mailed May 23, 2013, 8 pages.
Bechtold, et al., "Perfectly Alternating Copolymer of Lactic Acid and Ethylene Oxide as a Plasticizing Agent for Polylactide," Macromolecules 34: 8641-8648 (2001).
Burch, et al., "Synthesis of Cyclic Oligoesters and Their Rapid Polymerization to High Molecular Weight," Macromolecules 33: 5053-5064 (2000).
Carey, Francis A. and Sundberg, Richard J., Advanced Organic Chemistry, Second Edition, Part B: Reactions and Synthesis Plenum Press, NY (1983) p. 539-552.

(Continued)

*Primary Examiner* — Samantha Shterengarts
*Assistant Examiner* — Matt Mauro
(74) *Attorney, Agent, or Firm* — Cantor Colburn LLP

(57) ABSTRACT

Disclosed herein is a polyketal adduct obtained by forming an ester between a hydrocarbon polyol and a ketocarboxylic acid to produce an intermediate polyketocarboxylic ester. The intermediate polyketocarboxylic ester can be purified via crystallization to achieve purities of greater than 99.0% and then ketalized to produce the polyketal adduct, which can be used in polymer compositions. The polyketal adduct I is obtained at high purity and at high yield.

17 Claims, No Drawings

(56) References Cited

FOREIGN PATENT DOCUMENTS

| WO | 2009032905 A1 | 3/2009 | |
| WO | WO 2009048874 A1 | * | 4/2009 |

OTHER PUBLICATIONS

Chopade, et al., "Acetalization of ethylene glycol with formaldehyde using cation-exchange resins as catalysts: batch versus reactive distillation," Reactive and Functional Polymers 34: 37-45 (1997).

Clarkson, et al., "Continuous Reactor Technology for Ketal Formation: An Improved Synthesis of Solketal," Organic Process Research & Development 5: 630-635 (2001).

Clerici, Angelo, et al., "Efficient Acetalisation of Aldehydes Catalyzed by Titanium Tetrachloride in a Basic Medium", Tetrahedron 54 (1998) p. 15679-15690.

Deutsch, et al., Investigations on heterogeneously catalysed condensations of glycerol to cyclic acetals, Journal of Catalysis 245: 428-435 (2007).

Gasparrini, F., "Synthesis of Dimethyl Acetals, Diethyl Acetals, and Cyclic Acetals Catalyzed by Aminopropylated Silica Gel Hydrocholoride(APSG-HCL)", Tetrahedron 40(9), (1984) p. 1491-1500.

Grajkowski, Andrzej et al., "Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group", J. Org. Chem, 2007, vol. 72, No. 3, 805-815.

Hiltunen, et al., Synthesis and Characterization of Lactic Acid Based Telechelic Prepolymers, Macromolecules 29: 8677-8682 (1996).

Hoydoncks, et al., "Esterification and transesterification of renewable chemicals," Topics in Catalysis 27(1-4): 83-96 (2004).

Imwinkelried, et al., "Diisopropyl (2S,3S)-2,3-0-Isopropylidenetartrate [1,3-Dioxolane-4,5-dicarboxylic acid, 2,2-dimethyl-, bis(1-methylethyl)ester, (4R-trans)-]," Organic Syntheses 8: 201-230 (1993).

Transmittal and International Search Report for PCT/US2011/060450, mailed May 29, 2012, 7 pages.

Written Opinion of the International Searching Authority for PCT/US2011/060450, mailed May 29, 2012, 6 pages.

Kim, et al., "Preparation of High-Molecular-Weight Poly(L-lactic acid)-Based Polymers Through Direct Condensation Polymerization in Bulk State," Journal of Applied Polymer Science 100: 466-472 (2006).

Li, Tong-Shuang, et al., "Montmorillonite Clay Catalysis. Part 2. An Efficient and Convenient Procedure for the Preparation of Acetals Catalysed by Montmorillonite K-10," J. Chem Research (S) 26-27 (1997).

Meher, et al., "Technical aspects of biodiesel production by transesterification—a review," RSER 194: 1-21 (2004).

Meskens, Frans A. J., Methods for the Preparation of Acetals from Alcohols or Oxiranes and Carbonyl Compounds, Synthesisn (1981) 501-522.

Nagahata, et al., "Solid-Phase Thermal Polymerization of Macrocyclic Ethylene Terephthalate Dimer Using Various Transesterification Catalysts," Journal of Polyer Science: Part A: Polymer Chemistry 38: 3360-3368 (2000).

Nagata, et al., "Synthesis and Applications of [2-Methyl-2(oxoalkyl)-1,3-dioxolan-4-yl] methyl Acrylates for Photocrosslinking Agent," Osaka Kogyo Gijutsu Shikensho Kiho 37(1): 8-16 (1986).

Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).

Newman, et al.,"Kinetic and Equilibrium Studies of Cyclic Ketal Formation and Hydrolysis," The Journal of the American Oil Chemist's Society 80: 6350-6355 (1958).

Otera, Junzo, Esterification, Methods, Reactions, and Applications, Wiley-VCH Verlag GmbH & Co., (2003) p. 1-19.

Pang, et al., "Review of conventional and novel polymerization processes for polyesters," Prog. Polym. Sci. 31: 1009-1037 (2006).

Pasto, D. J. and Serve, M. P., "Neighboring Group Participation by Carbonyl Oxygen", J. Amer. Chem. Soc., 87(7) (1965) 1515-1521.

Patel, et al., "Ketalization of ketones with diols catalyzed by metal (IV) phosphates as solid acid catalysts," Journal of Molecular Catalysis A: Chemical 194: 267-271 (2003).

Piantadosi, et al., "The Preparation of Cyclic Glycerol Acetals by Transacetalation," Journal of the American Chemical Society 80: 6613-6617 (1958).

Showler, et al., "Condensation Products of Glycerol with Aldehydes and Ketones. 2-Substituted m-Dioxan-5-OLS and 1,3-dioxolane-4-methanols," Chem. Rev. 67: 427-440 (1967).

Smith, et al., "The gem-Dialkyl Effect. III. Kinetic and Equilibrium Studies of Steroid Cyclic Ketal Formation and Hydrolysis," Journal of the American Chemical Society 90(5): 1253-1257 (1968).

Sodergard, et al., "Properties of lactic acid based polymers and their correlation with composition," Prog. Polym. Sci. 27: 1123-1163 (2002).

Vermylen, et al., "Study of the Thermal Evolution of the Cyclic-Oligomer Formation in a Cyclic-Oligomer-Free PET," Journal of Polymer Science: Part A: Polymer Chemistry 38: 416-422 (2000).

Wang, et al., "An efficient procedure for protection of carbonyls catalyzed by sulfamic acid," Journal of Molecular Catalysis A: Chemical 233: 121-126 (2005).

Wood, et al., "Cyclic polyesters: 1. Preparation by a new synthetic method, using polymer-supported reagants," Polymer 34(14): 3052-3058 (1993).

Xu, et al., "The monoblocking of symmetrical diketones on insoluble polymer supports," Can. J. Chem. 61: 1405-1409 (1983).

Yamada, Tatsuhiko et al., "Characterization of the products resulting from ethylene glycol liquefaction of cellulose", J. Wood Sci. 2001, vol. 47, 458-464.

Carey, M.A., et al., "Rapid Method for Measuring the Hydroxyl Content of Polyurethane Polyols" (published on the internet at http://www.polyurethane.org/s_api/doc_paper.asp?CE)=::1044 &DID=4060, accessed on Dec. 29, 2011.) 11 pages.

Hachihama, Yoshikazu; Hayashi, Izumi, "Studies on the Preparation of Plasticizers from Carbohydrate Sources", Technology Reports of the Osaka University (1953), 3, 191-200.

Chirila, Traian, "Cicloacetal-esteri penta-se hexaatomici", Revista de Chimie 28(8), 730-733 (1977) [with English abstract].

Gelas, Jacques and Thiallier, Andre, "Synthese du 4-oxo et de 4-hydroxy-3,6,8-trioxabicyclo[3.2.1]octanes", Carbohydrate Research 30(1), 1973, p. 21-34 1973 (with English abstract).

Grabarnick et al., On five—species; Mar. 2000; American Chemical Society; Chem Abstract 132: 308566, 2 pages.

Lenz et al.; poly(ester-acetals)—azelaaldehydate; May 1984; American Chemical Society; Chem Abstract 70:97280, 3 pages.

Lenz et al.; Structure—poly(acetals); May 1984; Macromolecules (1969), 2(2), 129-36.

Lenz et al.; Structure—repeating units; May 1984; American Chemical Society; Chem Abstract 72; 122322, 4 pages.

Ono et al, "Preparation, Surface-Active Properties and Acid Decomposition Profiles of a New 'Soap' Bearing a 1,3-Dioxolane Ring", JAOCS, vol. 70, No. 1, 1993, pp. 29-36.

European Search Report for European Application No. 08838076.1, Report Date Dec 5, 2014, 4 pages.

* cited by examiner

POLYKETAL ADDUCTS, METHODS OF MANUFACTURE AND USES THEREOF

CROSS-REFERENCE TO RELATED APPLICATION

This application claims the benefit under 35 U.S.C. 119(e) of U.S. Provisional Application Ser. No. 61/412,573, filed on Nov. 11, 2010, and U.S. Provisional Application Ser. No. 61/508,974 filed on Jul. 18, 2011, the entire contents of both applications being incorporated by reference herein in their entirety.

BACKGROUND

This disclosure relates to polyketal adducts. In particular, this disclosure relates to polyketal adducts and their utility as plasticizers.

Many chemical additives such as plasticizer compounds are generally derived from non-renewable, petroleum or natural gas derived feedstocks. Phthalate esters, particularly, dioctyl phthalate ester, butyl-benzyl phthalate ester, and diisononyl phthalate ester are industrially significant plasticizers useful for plasticizing many polymeric formulations. Examples of polymeric formulations that are plasticized by phthalates include poly(vinyl chloride) (PVC), polyethylene terephthalate ethylene (PET), and the like.

In addition to being derived from non-renewable feedstocks, some chemical additives, such as phthalates, are easily released into the environment. As plastics age and break down, the release of phthalates accelerates. Phthalates have been associated with endocrine disruption and metabolic interference, as well as changes in hormone levels in rodents. As a result, recent regulatory pressure has targeted phthalates for replacement due to the risks associated with their use.

SUMMARY

Accordingly, there remains a need in the art for biosourced chemical additives such as plasticizers for polymeric formulations. It is also desirable that such materials be synthesized economically in large volumes. A still further advantage would be manufacture of the chemical additives in higher purity.

Accordingly, in an aspect, the invention is a method for the manufacture of a biosourced polyketal adduct I

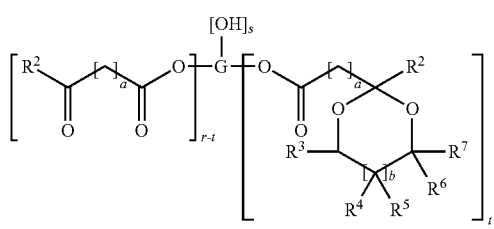

wherein
G is a hydrocarbon group having a valence of g, wherein g=2-12,
$R^2$ is each independently $C_1$-$C_6$ alkyl,
$R^3$ is each independently hydrogen or $C_1$-$C_6$ alkyl,
$R^4$ and $R^5$ are each independently hydrogen or $C_1$-$C_6$ alkyl,
$R^6$ is each independently
hydrogen or $C_1$-$C_6$ alkyl, or
$R^3$ and $R^6$ together with their directly attached carbons form a fused cycloaliphatic or aromatic ring having a total of 5-6 carbon atoms or 4-5 carbon atoms and 1-2 oxygen atoms,
$R^7$ is each independently hydrogen, $C_1$-$C_6$ alkyl, or $C_5$-$C_6$ cycloalkyl that is optionally substituted with an oxygen in the ring and further optionally substituted with 1-2—$OR^{10}$ wherein $R^{10}$ is $C_1$-$C_3$ alkyl,
a is each independently 0-3,
b is each independently 0 or 1
r-t=0-10,
s=0-10, and
t=2-12, provided that (r-t)+s+t=g,
the method comprising forming an ester between a hydrocarbon polyol II

$$G\text{-}[OH]_g \qquad\qquad II$$

and a ketocarboxy compound III in the presence of an ester-forming catalyst,

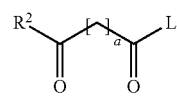

wherein each ketocarboxy compound III is the same or different, L is hydroxy, halide, or —$OR^{11}$ wherein $R^{11}$ is a $C_1$-$C_4$ alkyl, and the forming an ester is conducted with at least 0.75 equivalents of the ketocarboxy compound III per one equivalent of hydroxy group in the hydrocarbon polyol II, to form a polyketocarboxylic ester IV

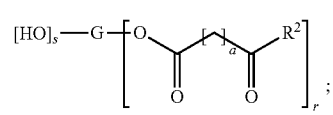

wherein s=0-10 and r=1-12, provided that s+r=g; and
ketalizing polyketocarboxylic ester IV with a molar excess of polyol V

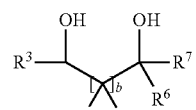

in the presence of a ketalization catalyst to provide the polyketal adduct I having less than 7 wt % of an oligomer; wherein the oligomers are reaction byproducts that have a molecular weight higher than the molecular weight of the polyketal adduct I.

In another aspect, a composition comprises (a) at least one of less than 1 ppm of a transition metal catalyst, less than 7 wt % of an oligomer, wherein the oligomers are reaction byproducts that have a molecular weight higher than the molecular weight of the polyketal adduct I, a polyketocarboxylic IV

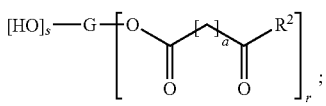

a hydroxy ketoester VI

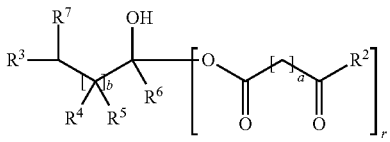

a hydroxy ketal ester VII

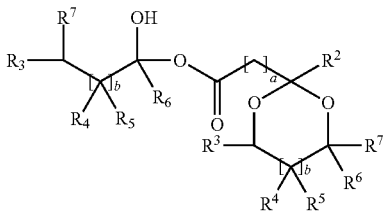

or a combination comprising at least one of the foregoing compounds IV, VI, and VII and (b) a polyketal adduct I

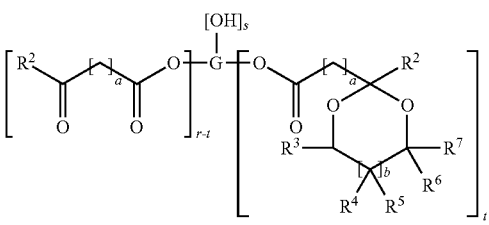

wherein in formulas I, IV, VI, and VII
G is a hydrocarbon group having a valence of g,
$R^2$ is each independently $C_1$-$C_6$ alkyl,
$R^3$ is each independently hydrogen or $C_1$-$C_6$ alkyl,
$R^4$ and $R^5$ are each independently hydrogen or $C_1$-$C_6$ alkyl,
$R^6$ is each independently
   hydrogen or $C_1$-$C_6$ alkyl, or
   $R^3$ and $R^6$ together with their directly attached carbons form a fused cycloaliphatic ring having a total of 5-6 carbon atoms or 4-5 carbon atoms and 1-2 oxygen atoms,
$R^7$ is each independently hydrogen, $C_1$-$C_6$ alkyl, or $C_5$-$C_6$ cycloalkyl that is optionally substituted with an oxygen in the ring and further optionally substituted with 1-2— $OR^{10}$ wherein $R^{10}$ is $C_1$-$C_3$ alkyl,
a is each independently 0-3,
b is each independently 0 or 1,
r-t=0-10,
s=0-10, and
t=2-12, provided that (r-t)+s+t=g.

Disclosed herein too is a composition comprising an organic polymer; and the polyketal adduct I.

In another aspect, articles comprising polymer formulations are also disclosed.

The invention is further illustrated by the following Detailed Description and Examples.

DETAILED DESCRIPTION

The inventors hereof have found that polyketal adducts I can be efficiently produced by a process wherein a hydrocarbon polyol II is esterified with a ketocarboxy compound III to produce an intermediate polyketocarboxylic ester. The esterifying is conducted with at least 0.75 equivalents of the ketocarboxy compound III per one equivalent of hydroxy group in the hydrocarbon polyol II. The polyketocarboxylic ester is then ketalized to produce the polyketal adduct I.

In a particularly advantageous aspect, both the hydrocarbon polyol II and the ketocarboxy compound III can be biosourced.

The inventors have further found that purifying the intermediate polyketocarboxylic ester IV before ketalization results in higher purity polyketal adducts I and further, that by varying the reaction conditions during ketalization both high purity and high yield polyketal adducts I can be obtained. Thus, in an embodiment, the intermediate polyketocarboxylic ester is isolated, for example by crystallization or distillation, to produce a highly purified polyketal adduct I in higher purity and/or at higher yields than those produced if the polyketocarboxylic ester was not isolated. Alternatively, in another advantageous aspect, the process can proceed continuously without isolation of the intermediate polyketocarboxylic ester. In still another advantageous feature, the polyketal adduct I can be obtained in high purity, for example in the absence of a higher molecular weight oligomeric species or a catalyst.

The method for the manufacture of a polyketal adduct I comprises esterifying a hydrocarbon polyol II $$G\text{-}[OH]_g \qquad \text{II}$$

where G is a hydrocarbon group having a valence of g, wherein g is 2 to 12, specifically 2 to 10, more specifically 3 to 8, or 3 to 6. In an embodiment, G is a $C_2$-$C_{32}$ hydrocarbon containing 1 or more straight chain, branched or cyclic groups that can be saturated, unsaturated, aromatic, or substituted with up to 12 ether oxygens; more specifically, G is a $C_2$-$C_{12}$ alkylene, $C_5$-$C_8$ cycloalkylene, or $C_6$-$C_{12}$ arylene, optionally substituted with up to 5 ether oxygens; or G is a $C_2$-$C_8$ alkylene, $C_2$-$C_8$ alkylene, $C_5$-$C_8$ cycloalkylene, or $C_6$-$C_{12}$ arylene, or $C_4$-$C_{16}$ alkyleneoxy group of the formula —$(R^{12}O)_qR^{12}$— wherein each $R^{12}$ is independently ethylene, 1,3-propylene, or 1,2-propylene and q=1-7; or a $C_2$-$C_6$ alkylene; or ethylene, or 1,4-butylene, or 1,6-hexylene.

A combination of hydrocarbon polyols II can be used in the manufacture of polyketal adduct I, such that each hydrocarbon polyol II can be the same or different, and each g and each G in polyketal adduct I or its byproducts or intermediates can be the same or different. In a specific embodiment, each hydrocarbon polyol II is the same, and thus each g and each G in polyketal adduct I or its byproducts or intermediates is the same.

Hydrocarbon polyol II is esterified with at least 0.75 equivalents of the ketocarboxy compound III per one equivalent of a hydroxy group in the hydrocarbon polyol II

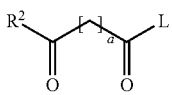

wherein each ketocarboxy compound III is the same or different. $R^2$ in ketocarboxy compound III is $C_1$-$C_6$ alkyl, specifically a $C_1$-$C_4$ alkyl, more specifically a $C_1$-$C_2$ alkyl, even more specifically methyl. Further in formula III, a=0-3, more specifically 1-2, still more specifically 2. When a is 0, a single bond connects the two carbonyl groups. Also in ketocarboxy compound III, L is a hydroxy, halide, or —$OR^{11}$ wherein $R^{11}$ is a $C_1$-$C_3$ alkyl. In a specific embodiment L is hydroxy.

A combination of ketocarboxy compounds III can be used, such that each ketocarboxy compound III may be the same or different, and each a and each $R^2$ in polyketal adduct I or its byproducts or intermediates may be the same or different. In a specific embodiment, each ketocarboxy compound III is the same, and thus each a and each $R^2$ in polyketal adduct I or its byproducts or intermediates is the same.

Forming an ester (esterification) occurs in the presence of no added catalyst (the ketocarboxy compound III can function as a catalyst), an acid esterforming catalyst, or a base ester-forming catalyst if L is a halide as described in further detail below. Esterification produces a polyketocarboxylic ester IV

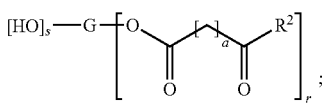

wherein $R^2$ and a are as in the ketocarboxy compound III, s is 0-10, specifically 1-8, more specifically 2-4, r is 1-12, specifically 2 to 10, more specifically 3 to 8, and s+r=g, which is the valence of hydrocarbon polyol II. As described below, this product can be used as synthesized or further purified.

Forming an ester is followed by ketalizing the polyketocarboxylic ester IV with a molar excess of a polyol V

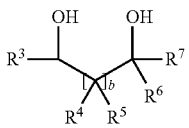

wherein a combination of different polyols V can be used. A combination of polyols V can be used, such that each polyol V may be the same or different, and each variable b, $R^3$, $R^4$, $R^5$, $R^6$, and $R^7$, in polyketal adduct I or its byproducts or intermediates may be the same or different. In a specific embodiment, each polyol V is the same, and thus each variable, b, $R^3$, $R^4$, $R^5$, $R^6$, and $R^7$ in polyketal adduct I or its byproducts or intermediates is the same.

In formula V, $R^3$ is hydrogen or $C_1$-$C_6$ alkyl, specifically hydrogen or $C_1$-$C_3$ alkyl, more specifically hydrogen. $R^4$ and $R^5$ in formula V are each independently hydrogen or $C_1$-$C_6$ alkyl, specifically hydrogen or $C_1$-$C_3$ alkyl.

$R^6$ in formula V is hydrogen or $C_1$-$C_6$ alkyl, specifically hydrogen or $C_1$-$C_3$ alkyl. Further, $R^3$ and $R^6$ together with their directly attached carbons can form a fused cycloaliphatic or aromatic ring having a total of 5-6 carbon atoms or 4-5 carbon atoms and 1-2 oxygen atoms, specifically a fused cycloaliphatic or aromatic ring having a total of 5-6 carbon atoms.

$R^7$ in formula V is hydrogen, $C_1$-$C_6$ alkyl, or $R^7$ is $C_5$-$C_6$ cycloalkyl that is optionally substituted with an oxygen in the ring and further optionally substituted with 1-2—$OR^{10}$ wherein $R^{10}$ is $C_1$-$C_3$ alkyl. In a specific embodiment, $R^7$ is hydrogen or $C_1$-$C_4$ alkyl, more specifically hydrogen or $C_1$-$C_3$ alkyl, still more specifically methyl.

In formula V b is 0 or 1. When b is 0, the carbon bearing $R^3$ is directly linked to the carbon bearing $R^6$ and $R^7$.

Ketalization in the presence of a ketalization catalyst provides the polyketal adduct I

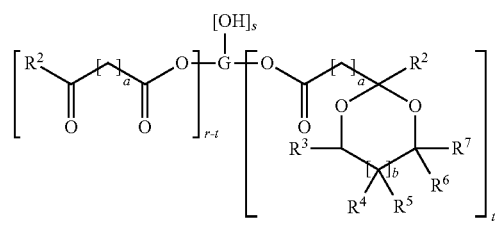

wherein each of G, $R^2$, $R^3$, $R^4$, $R^5$, $R^6$, and $R^7$, a, b, r, s, and t are independently selected and as defined in formulas II, III, IV, and V. In addition to the polyketal adduct I, the manufacture of polyketal adduct I can also provide certain byproducts, including a hydroxyl ketoester VI,

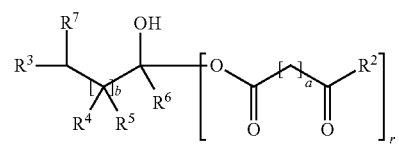

a hydroxyl ketal ester VII,

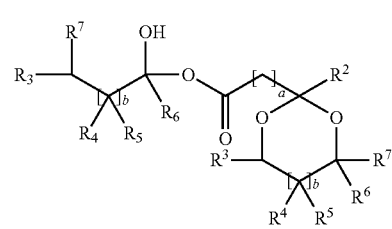

or a combination thereof, wherein each of $R^2$, $R^3$, $R^4$, $R^5$, $R^6$, and $R^7$, a, and b are independently selected and as defined in formulas II, III, IV, and V. The hydroxyl ketoester VI and the a hydroxyl ketal ester VII can themselves be isolated, in a purity of at least 80 wt %, at least 90 wt %, at least 95 wt %, at least 98 wt %, or at least 99 wt %.

In a specific embodiment, particularly when a molar excess of polyol V is used, the polyketal adduct I is a fully ketalized species of the formula Ia

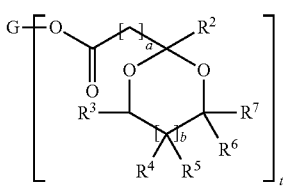

Ia wherein each of G, $R^2$, $R^3$, $R^4$, $R^5$, and $R^7$, a, b, and t are as defined in formula I.

With reference to each of formulas II, III, IV, V, VI, VII, and polyketal adduct I and Ia,
- G is a hydrocarbon group having a valence of g,
- $R^2$ is each independently $C_1$-$C_6$ alkyl,
- $R^3$ is each independently hydrogen or $C_1$-$C_6$ alkyl,
- $R^4$ and $R^5$ are each independently hydrogen or $C_1$-$C_6$ alkyl
- $R^6$ is each independently hydrogen or $C_1$-$C_6$ alkyl, or $R^3$ and $R^6$ together with their directly attached carbons form a cycloaliphatic ring having a total of 5-6 carbon atoms or 4-5 carbon atoms and 1-2 oxygen atoms,
- $R^7$ is each independently hydrogen, $C_1$-$C_6$ alkyl, or $C_5$-$C_6$ cycloalkyl that is optionally substituted with an oxygen in the ring and further optionally substituted with 1-2—$OR^{10}$ wherein $R^{10}$ is $C_1$-$C_3$ alkyl,
- a is each independently 0-3,
- b is each independently 0 or 1,
- r-t=0-10,
- s=0-10, and
- t=2-12, provided that (r-t)+s+t=g.

In this embodiment, each equivalent of ketocarboxy compound III and polyol V can be the same or different, and thus each variable, e.g., b or each $R^2$, may be the same or different. Preferably, each equivalent of ketocarboxy compound III and polyol V is the same and thus each variable, e.g., each b or each $R^2$, is the same.

In another specific embodiment with reference to each of formulas II, III, IV, V, VI, VII, and polyketal adduct I and Ia,
- G is a $C_2$-$C_{32}$ hydrocarbon containing 1 or more straight chain, branched or cyclic groups that can be saturated, unsaturated, aromatic, or substituted with up to 12 ether oxygens,
- $R^2$ is each independently $C_1$-$C_3$ alkyl,
- $R^3$ is each independently hydrogen or $C_1$-$C_3$ alkyl,
- $R^4$ and $R^5$ is each hydrogen or $C_1$-$C_3$ alkyl,
- $R^6$ is each independently hydrogen or $C_1$-$C_3$ alkyl, or $R^3$ and $R^6$ together with their directly attached carbons form a fused cycloaliphatic ring having a total of 5-6 carbon atoms or 4-5 carbon atoms and 1-2 oxygen atoms,
- $R^7$ is each independently hydrogen or $C_1$-$C_4$ alkyl,
- a is each independently 0-3,
- b is each independently 0 or 1,
- r-t=0-10,
- s=0-10, and
- t=2-12.

In this embodiment, each equivalent of ketocarboxy compound III and polyol V can be the same or different, and thus each variable, e.g., b or each $R^2$, may be the same or different. Preferably, each equivalent of ketocarboxy compound III and polyol V is the same and thus each variable, e.g., each b or each $R^2$, is the same.

In yet another specific embodiment with reference to each of formulas II, III, IV, V, VI, VII, and polyketal adduct I, and Ia, where each equivalent of ketocarboxy compound III and polyol V is the same,
- G is a $C_2$-$C_8$ alkylene, $C_2$-$C_8$ alkylene, $C_5$-$C_8$ cycloalkylene, or $C_6$-$C_{12}$ arylene, or $C_4$-$C_{16}$ —$(R^{12}O)_qR^{12}$— wherein each $R^{12}$ is independently ethylene, 1,3-propylene, or 1,2-propylene,
- each $R^2$ is the same $C_1$-$C_3$ alkyl,
- each $R^3$ is the same hydrogen or $C_1$-$C_3$ alkyl,
- each $R^4$ is the same hydrogen or $C_1$-$C_3$ alkyl,
- each $R^5$ is the same hydrogen or $C_1$-$C_3$ alkyl,
- each $R^6$ is the same hydrogen or $C_1$-$C_3$ alkyl, or $R^3$ and $R^6$ together with their directly attached carbons form a fused cycloaliphatic or aromatic ring having a total of 5-6 carbon atoms or 4-5 carbon atoms and 1-2 oxygen atoms,
- each $R^7$ is the same hydrogen or $C_1$-$C_4$ alkyl,
- a=0-3,
- b=0 or 1,
- r-t=0-10,
- s=0-10, and
- t=2-12

In yet another specific embodiment with reference to each of formulas II, III, IV, V, VI, VII, and polyketal adduct I, where each equivalent of ketocarboxy compound III and polyol V and Ia is the same,
- G is a $C_2$-$C_{12}$ alkylene optionally substituted with up to 5 ether oxygens,
- each $R^2$ is the same $C_1$-$C_2$ alkyl,
- each $R^3$ is the same hydrogen or $C_1$-$C_3$ alkyl,
- each $R^4$ is the same hydrogen or $C_1$-$C_3$ alkyl,
- each $R^5$ is the same hydrogen or $C_1$-$C_3$ alkyl,
- each $R^6$ is the same hydrogen or $C_1$-$C_3$ alkyl,
- each $R^7$ is the same hydrogen or $C_1$-$C_4$ alkyl,
- a=1-2,
- b=0 or 1,
- r-t=0-10,
- s=0-10, and
- t=2-12.

In still another specific embodiment, the polyketal adduct I is a fully ketalized adduct wherein (r-t)=0 and s=0, i.e., a polyketal adduct Ia

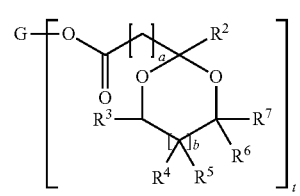

Ia wherein
- G is a $C_2$-$C_{12}$ alkylene optionally substituted with up to 5 ether oxygens,
- $R^2$ is each independently $C_1$-$C_2$ alkyl,
- $R^3$ is each independently hydrogen or $C_1$-$C_3$ alkyl,
- $R^4$ is each independently hydrogen or $C_1$-$C_3$ alkyl,
- $R^5$ is each independently hydrogen or $C_1$-$C_3$ alkyl,
- $R^6$ is each independently hydrogen or $C_1$-$C_3$ alkyl,
- $R^7$ is each independently hydrogen or $C_1$-$C_4$ alkyl,
- a is each independently 1-2,
- b is each independently 0 or 1, and
- t=2-12, specifically 2 to 6, specifically 2.

In another specific embodiment, the hydrocarbon polyol is an alkylene diol IIa

HO-G-OH     IIa wherein G is a $C_2$-$C_{32}$ alkylene, specifically a $C_2$-$C_6$ alkylene, specifically a $C_2$, $C_4$, or $C_6$ alkylene. The diols ethylene glycol, 1,4-butanediol (BDO), and 1,6-hexanediol can be specifically mentioned. The alkylene diol is esterified by reaction with at least 0.75 or more equivalents of a ketocarboxylic acid (levulinic acid) IIIa

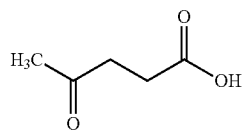
IIIa in the presence of an acid esterification catalyst, to produce a diketocarboxylic ester IVa

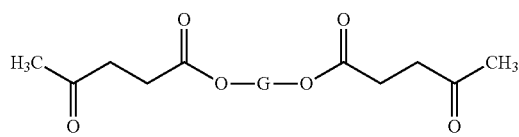
IVa wherein G is a $C_2$-$C_6$ alkylene, specifically a $C_2$-$C_4$ alkylene, more specifically 1,4-butylene. Ketalizing the diketocarboxylic ester IVa with a polyol Va,

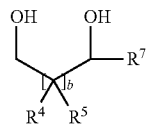
Va wherein $R^4$ is hydrogen or $C_1$-$C_3$ alkyl, $R^5$ is hydrogen or $C_1$-$C_3$ alkyl, $R^7$ is hydrogen or $C_1$-$C_3$ alkyl, and b=0 or 1 in the presence of a ketalization catalyst provides a polyketal adducts Ib, Ic, or Id

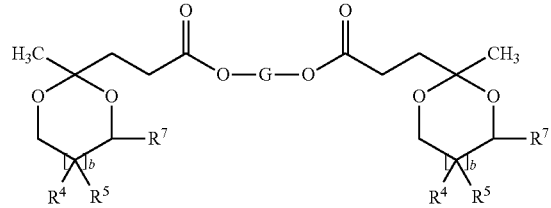
Ib

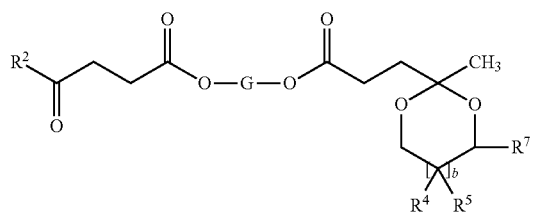
Ic

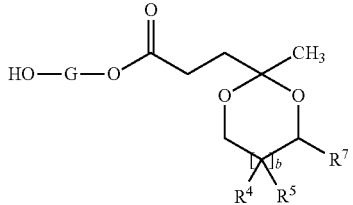
Id wherein
G is a $C_2$-$C_{32}$ alkylene, specifically a $C_2$-$C_6$ alkylene, specifically a $C_2$, $C_4$, or $C_6$ alkylene,
$R^2$ is each independently $C_{1-2}$ alkyl,
$R^4$ is each independently hydrogen or $C_1$-$C_3$ alkyl,
$R^5$ is each independently hydrogen or $C_1$-$C_3$ alkyl
$R^7$ is each independently hydrogen or $C_1$-$C_3$ alkyl,
b is each independently 0 or 1, and
s=1-11, specifically 1-5, more specifically 1-2.

In another specific embodiment, the hydrocarbon polyol is an alkylene diol IIb

HO-G-OH      IIa wherein G is a $C_2$-$C_6$ alkylene, specifically a $C_2$, $C_4$, or $C_6$ alkylene. The alkylene diol IIa is esterified by reaction with at least 0.75 equivalents of a ketocarboxylic acid (levulinic acid) IIIa per 1 equivalent of a hydroxy group in the hydrocarbon polyol II

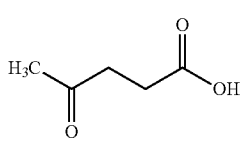
IIIa in the presence of an acid esterification catalyst, to produce a diketocarboxylic ester IVa

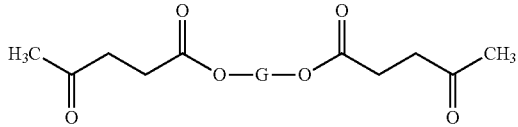
IVa wherein G is a $C_2$-$C_6$ alkylene, specifically a $C_2$-$C_4$ alkylene, more specifically ethylene, 1,4-butylene, or 1,6-hexylene. Ketalizing the diketocarboxylic ester IVa with a 1,2-diol Vb

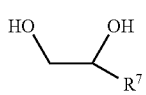
Vb wherein $R^7$ is hydrogen or $C_1$-$C_3$ alkyl, specifically methyl, in the presence of a ketalization catalyst provides the polyketal adduct Ie, If, Ig, or a combination comprising at least one of the foregoing adducts,

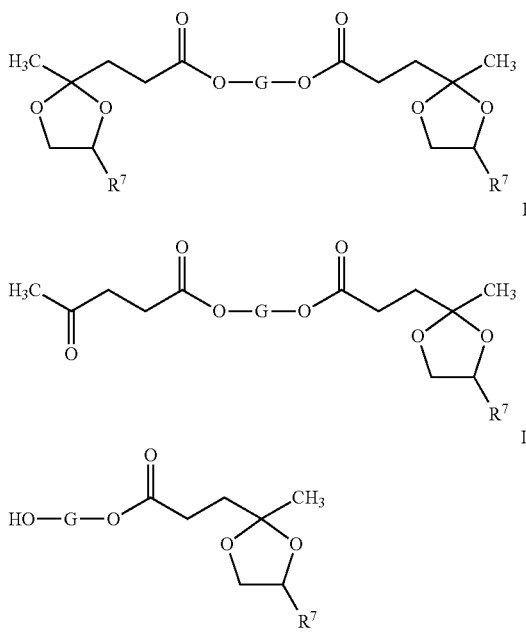

wherein G is a $C_2$-$C_6$ alkylene, specifically a $C_2$-$C_4$ alkylene, more specifically ethylene, 1,4-butylene, or 1,6-hexylene, and $R^7$ is hydrogen or $C_1$-$C_3$ alkyl, specifically methyl.

The LPK-alkylene-LPK adduct Ih has the formula

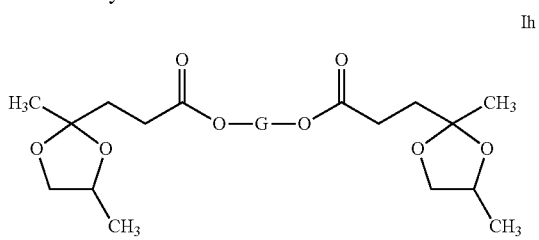

wherein is G is a $C_2$-$C_6$ alkylene, specifically ethylene, 1,4-butylene, or 1,6-hexylene. The partially ketalized LA-alkylene-LPK adduct Ii has the formula

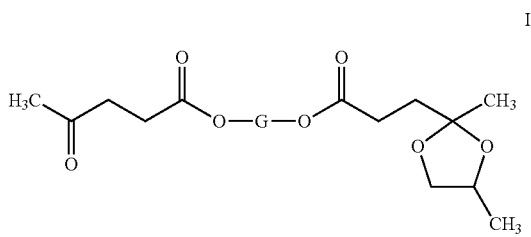

wherein G is a $C_2$-$C_6$ alkylene, specifically ethylene, 1,4-butylene, or 1,6-hexylene. The partially ketalized hydroxyalkylene-LPK adduct Ij has the formula

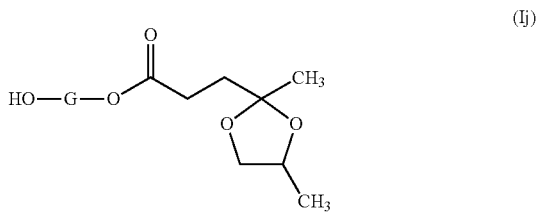

wherein G is a $C_2$-$C_6$ alkylene, specifically ethylene, 1,4-butylene, or 1,6-hexylene.

The relative amounts of each type of polyketal adduct I (i.e., the relative amounts of polyketal adduct Ib, Ic, and Id, or polyketal adduct Ie, If, Ig, or polyketal adduct Ih, Ig, and Ij in a given composition can be adjusted by adjusting the reaction conditions, including relative ratios of starting materials as further described below.

In a method of manufacturing the polyketal adduct I, the hydrocarbon polyol II and 0.75 or more, for example 1, 1.2, 2, 3, or 4 or more equivalents of a ketocarboxy compound III (per 1 equivalent of a hydroxy group in the hydrocarbon polyol II) and an acid catalyst are charged to a reactor. In an embodiment, the molar ratio of the equivalents of ketocarboxy compound III to the equivalents of hydroxy moieties in the hydrocarbon polyol II is compound III are used, specifically 1.0 to 1.75 equivalents of ketocarboxy compound III greater than or equal to about 0.75:1, specifically greater than or equal to about 0.85:1 and more specifically greater than or equal to about 1:1. In an embodiment, 0.75 to 2 equivalent of the ketocarboxy per one equivalent of hydroxy moieties in the hydrocarbon polyol II.

The esterification and/or ketalization is conducted in the presence of a catalyst, for example base if used for the esterification, such as a tertiary amine, a quaternary ammonium hydroxide, a metal oxide, or a metal hydroxide. In an embodiment the catalyst for esterification and ketalization is an acid catalyst, which can be either a Lewis or Brønsted-Lowry acid. Acid catalysts that are known homogeneous catalysts for either ketal formation or esterification or transesterification reactions can be used, for example strong protic acid catalysts, e.g., Brønsted-Lowry acids that have a Ka of 55 or greater. Examples of strong protic acid catalysts include sulfuric acid, arylsulfonic acids, and hydrates thereof such as p-toluenesulfonic acid monohydrate, methane sulfonic acid, camphor sulfonic acid, dodecyl benzene sulfonic acid, perchloric acid, hydrobromic acid, hydrochloric acid, 2-naphthalene sulfonic acid, and 3-naphthalene sulfonic acid. In other embodiments, weak protic acid catalysts, e.g., having a Ka of less than 55, can be used, for example phosphoric acid, levulinic acid, orthophosphoric acid, polyphosphoric acid, and sulfamic acid. Aprotic (Lewis acid) catalysts can include, for example, titanium tetraalkoxides, aluminum trialkoxides, tin II alkoxides, carboxylates, organo-tin alkoxides, organo-tin carboxylates, and boron trifluoride. A combination comprising any one or more of the foregoing acid catalysts can be used. In some embodiments, the method employs a substantially nonvolatile acid catalyst such that the acid does not transfer into the distillate, such as sulfuric or sulfamic acid. In an exemplary embodiment, the homogenous catalyst is camphor sulfonic acid, dodecyl benzene sulfonic acid, sulfuric acid, or hydrochloric acid.

Instead of, or in addition to the homogenous acid catalyst, a heterogenous acid catalyst can be used, where the acid catalyst is incorporated into, onto, or covalently bound to, a solid support material such as resin beads, membranes, porous carbon particles, zeolite materials, and other solid supports. Many commercially available resin-based acid catalysts are sold as ion exchange resins. One type of useful ion exchange resin is a sulfonated polystyrene/divinyl benzene resin, which supplies active sulfonic acid groups. Other commercial ion exchange resins include LEWATIT® ion exchange resins sold by the Lanxess Company of Pittsburgh, Pa.; DOWEX™ ion exchange resins sold by the Dow Company of Midland, Mich.; and AMBERLITE® and AMBERLYST® ion exchange resins sold by the Dow Company of Midland, Mich. In embodiments, AMBERLYST® 15, AMBERLYST® 35, AMBERLYST® 70 are used. In these embodiments, the resin-based catalyst is washed with water, and subsequently, an alcohol, such as methanol or ethanol, and then dried prior to use. Alternatively, the resin is not washed before its first use. In embodiments, NAFION® resins (from DuPont in Wilmington, Del.) can also be used as heterogeneous catalysts in neat form or filled with silica. In use, the heterogenous catalysts are added to a reaction mixture, thereby providing a nonvolatile source of acid protons for catalyzing the reactions. The heterogenous catalysts can be packed into columns and the reactions carried out therein. As the reagents elute through the column, the reaction is catalyzed and the eluted products are free of acid. In other embodiments, the heterogenous catalyst is slurried in a pot containing the reagents, the reaction is carried out, and the resulting reaction products filtered or distilled directly from the resin, leaving an acid-free material.

The amount of acid catalyst is about 2 to 20,000 parts per million (ppm), specifically about 10 to about 10,000 ppm, specifically about 20 to about 5000 ppm, and more specifically about 30 to about 2500 ppm, relative to the total weight of the reactants. In this case, the reactants are the sum of hydrocarbon polyol II and the 0.75 or more equivalents of a ketocarboxy compound III.

When camphor sulfonic acid is used as the acid catalyst to produce the polyketal adduct I, it is used in amounts of about 5 to 5,000 parts per million (ppm), specifically about 10 to about 1000 ppm, specifically about 15 to about 800 ppm, and more specifically about 20 to about 600 ppm, relative to the total weight of the reactants. In this case, the reactants are the sum of hydrocarbon polyol II and the 0.75 or more equivalents of a ketocarboxy compound III.

The acid catalyst can be charged directly into the reactant mixture comprising the hydrocarbon polyol II and the ketocarboxy compound III or alternatively it can be diluted in water or one of the reactants prior to being charged into the reactant mixture. The acid catalyst can be diluted to about 0.01N to about 5N, specifically about 0.1N to about 4N, and more specifically about 0.5N to about 3N prior to introduction into the reactant mixture. The dilute acid catalyst can be continuously added to the reactant mixture throughout the course of the reaction or alternatively it can be added instantaneously to the reactant mixture in a single charge.

In an embodiment, the polyketal adduct, the hydrocarbon polyol II and the ketocarboxy compound III are charged to the reactor. The reaction to produce the polyketal adduct can be conducted in either a batch reactor, a continuous reactor or in a semicontinuous reactor. It is desirable for the reactor to have heating, cooling, agitation, condensation, and distillation facilities.

In an embodiment, the batch reactor for producing the polyketal adducts can comprise a single continuous stirred tank reactor in fluid communication with a reboiler that is fitted with a distillation column. In another embodiment, the system (not shown) for producing the polyketal adduct I can comprise a single continuous stirred tank reactor that is fitted with a distillation column. The distillation column is used to remove excess reactants and to distill the water condensate from the reaction.

In a batch reactor, the reactants and catalyst are charged to the reactor in batches and the product is extracted from the reactor in batches only after the reaction has been completed to an extent of about 80% or more. While a batch reactor can be used to react the reactants under a variety of different conditions, it is desirable to use a batch reactor when the product is manufactured by introducing the acid catalyst into the reactor in one charge. An exemplary batch reactor is a stainless steel or Hastelloy-type reactor. An example of a batch reactor is a continuous stirred tank reactor. It is desirable for the batch reactor to be equipped with distillation facilities for further purification of the product. The reaction to produce the polyketal adduct I can be conducted in a single reactor or in plurality of batch reactors. In an embodiment, the esterification can be conducted in a batch reactor, while the ketalization can be conducted in the same or in a second batch reactor.

In a continuous reactor system the reactants are charged to a first reactor. When the conversion of reactants to products is measured to be greater than or equal to about 50%, a portion of the product mixture from the first reactor is subjected to additional finishing processes in a second reactor, while at the same time additional reactants and catalyst are continuously being charged to the first reactor to be converted into the polyketal adduct I. A continuous reactor system generally employs a plurality of reactors in series or in parallel so that various parts of the process can be conducted in different reactors simultaneously.

The reactor can comprise a plurality of reactors (e.g., a multistage reactor system) that are in fluid communication with one another in series or in parallel. The plurality of reactors are used to react the hydrocarbon polyol II with the ketocarboxy compound III, to recycle the reactants and to remove unwanted byproducts and impurities so as to obtain a polyketal adduct I that is stable and has a long shelf life. In an embodiment, a portion of the plurality of reactors can be used primarily to react reactants to manufacture the polyketal adduct I, while another portion of the plurality of reactors can be used primarily to isolate the polyketocarboxylic ester IV and yet another portion of the plurality of reactors can be used to produce the polyketal adduct I or to remove the residual catalyst and other byproducts that can hamper the formation of a stable product that has good shelf stability.

In a specific embodiment, the esterification of the hydrocarbon polyol II with the ketocarboxy compound III to produce a polyketocarboxylic ester IV is conducted in a batch reactor. For example, in the manufacture of the polyketocarboxylic ester IV, a hydrocarbon polyol II and the ketocarboxy compound III are charged to the batch reactor along with the acid catalyst. The contents of the batch reactor are heated while being subjected to agitation. Volatile reactants or byproducts are collected in a condenser that is in fluid communication with the batch reactor. The polyketocarboxylic ester IV can be isolated from unreacted reactants and other reaction byproducts prior to the ketalizing. In an embodiment, the polyketocarboxylic ester IV is isolated via crystallization or distillation. In another embodiment, the polyketocarboxylic ester IV is recrystallized prior to ketalizing.

The batch reactor can be heated, for example to a temperature of about 110 to about 260° C., specifically about 150 to about 250° C., and specifically about 160 to about 240° C. to facilitate the esterification of the hydrocarbon polyol II by the ketocarboxy compound III. The esterification can be carried out under a blanket of an inert gas (e.g., argon, nitrogen, and the like) or alternatively can be carried out in a vacuum. The reactor can be subjected to a vacuum of about 5 to less than 760 torr, specifically about 10 to about 500 torr, more specifically about 10 to about 100 torr.

Upon completion of the esterification in the batch reactor, the reaction solution is cooled, which in some embodiments results in crystallization of the polyketocarboxylic ester IV. The crystalline polyketocarboxylic ester IV can be washed in a first solvent to remove any contaminants. The washed polyketocarboxylic ester IV can then be redissolved in a second solvent and recrystallized to produce a pure form of the polyketocarboxylic ester IV. The first and the second solvent can be the same or different. In an embodiment, the first solvent is a protic solvent such as water, methanol, ethanol, or isopropanol, and the second solvent is water, methanol, ethanol, or isopropanol as well. In another embodiment, heating and cooling steps can be performed to conduct re-crystallization. In still another embodiment, the polyketocarboxylic ester IV is isolated from the reaction mixture by extraction and/or distillation. The pure form of the polyketocarboxylic ester IV can have a purity of greater than or equal to about 98%, specifically greater than or equal to about 99%, on a weight basis. The pure form of the polyketocarboxylic ester IVc wherein G is a $C_2$-$C_6$ alkylene, specifically a $C_2$, $C_4$, or $C_6$ alkylene, more specifically 1,4-butylene comprises white, shiny, spherical flakes or needle-shaped crystals.

The polyketocarboxylic ester IV is then ketalized with the polyol V to produce the polyketal adduct I. During the ketalization, excess polyol V is removed from the polyketal adduct I by distillation. Thus, the polyketocarboxylic ester IV, with or without purification as described above is then reacted with an excess of the polyol V in the presence of a second catalyst, in a ketalization reactor, which can be the same batch reactor or in a second batch reactor. The contents of the ketalization reactor are heated while being subjected to agitation to produce the polyketal adduct I. Following the passage of a suitable amount of time, the ketalization reactor is cooled and the reactants neutralized with a base. The reaction mixture is purified by filtration, and only optionally by distillation to obtain the polyketal adduct I.

As noted above, the contents of the ketalization reactor are heated while being subjected to agitation to produce the polyketal adduct. The contents of the ketalization reactor are heated to a temperature of about 60 to about 200° C., specifically about 70 to about 160° C., and specifically about 80 to about 140° C. to produce the polyketal adduct I. The ketalization reactor can be subjected to a vacuum of 5 to about 500 torr, specifically about 10 to about 100 torr.

Use of the foregoing processes can produce the polyketal adduct I containing less than or equal to about 0.001 to about 10 ppm sulfur-containing acid impurities, specifically about 0.002 to about 5 ppm sulfur-containing acid impurities, based on the total weight of the composition. In a particularly advantageous feature, such levels are obtainable without distillation of the polyketal adduct I after synthesis.

Alternatively, or in addition, the polyketal adduct I is obtained as a composition having less than or equal to about 7 weight percent (wt %) of an oligomeric side product, specifically less than or equal to about 5 wt % of an oligomeric side product, and more specifically less than or equal to about 1 wt %, based on the total weight of the polyketal adduct. "Oligomeric side products" includes undesired impurities with or without repeat units and having a molecular weight higher than the molecular weight of the polyketal adduct I. It is also desirable for the polyketal adduct I composition to have less than or equal to about 7 wt %, specifically less than or equal to about 5 wt %, and more specifically less than or equal to about 1 wt % of an oligomeric side product having a molecular weight of greater than or equal to about 500 Daltons, based on the total weight of the polyketal adduct composition.

In a particularly advantageous feature, such purities are obtainable without purification, e.g., without distillation of the polyketal adduct I after synthesis. Sulfur-containing and oligomeric impurities are present where the polyketal adduct I is synthesized by other methods, for example reaction of the ketalized ketocarboxylic ester with a polyol. The high purity products obtained by the present method are therefore new compositions that appear to not have been previously obtained.

In the alternative, or in addition, the composition comprising the polyketal adduct I contains essentially no transition metals. For example, the composition comprising polyketal adduct I contains, e.g., 0-10 parts per million by weight (ppm), specifically 0-5 ppm, and more specifically 0-1 ppm, 0-0.5 ppm of a total content of transition metals. In a specific embodiment, the polyketal adduct I contains less than 1 ppm of a total content of, cobalt, nickel, tin, antimony, titanium, zirconium, or aluminum. In a particularly advantageous feature, such low quantities of transition metal impurities are obtainable without purification, e.g., without distillation of the composition comprising polyketal adduct I after synthesis.

In an embodiment, the composition comprising polyketal adduct I contains less than or equal to about 1 wt % of an alcohol. It is desirable for the polyketal adduct I to be less than or equal to about 0.5 wt % alcohol, specifically less than or equal to about 0.1 wt % alcohol. In an embodiment, the alcohol is specifically ethanol.

In another embodiment, the composition comprising polyketal adduct I contains less than 1 wt % of other volatile organic byproducts, for example a $C_{1-4}$ alcohol or byproduct a $C_{1-4}$ alcohol.

because of the crystallization of the polyketocarboxylic ester IV. It is desirable for the polyketal adduct I to contain less than or equal to about 0.5 wt %, specifically less than or equal to about 0.1 wt % of other volatile organic byproducts The composition comprising polyketal adduct I can further comprise one or more intermediates or byproducts, including a polyketocarboxylic IV,

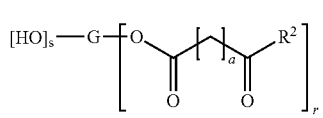

IV a hydroxy ketoester VI,

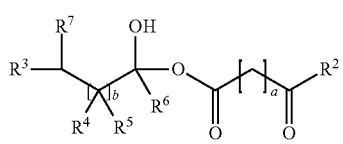

VI a hydroxy ketal ester VII,

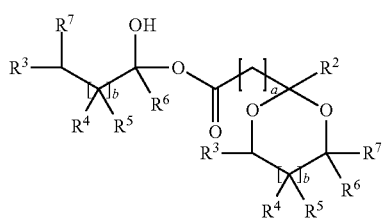

VII or a combination comprising at least one of the forgoing byproducts.

In a specific embodiment, during production of the composition comprising polyketal Ib, Ic, or Id, the byproducts include diketocarboxylic ester IVa, a hydroxy ketoester VIa, hydroxy ketal ester VIIa, or a combination comprising at least one of the foregoing compounds,

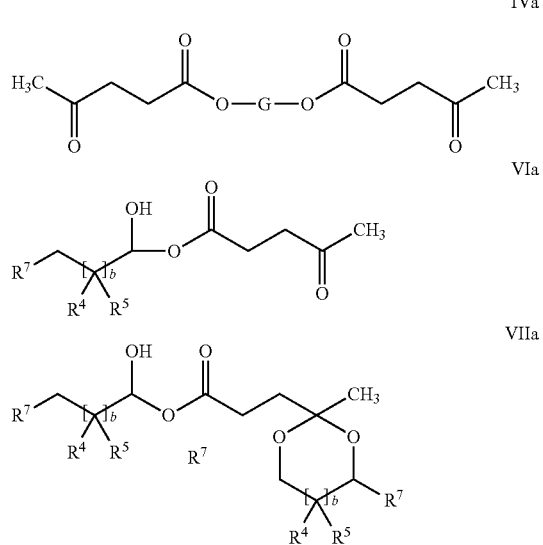

wherein G, $R^2$, $R^4$, $R^5$, $R^7$, and b are as defined in polyketal adducts Ib, Ic, or Id. The diketocarboxylic ester IVa, the hydroxy ketoester VIa, and the hydroxy ketal ester VIIa can themselves each be isolated, in a purity of at least 80 wt %, at least 90 wt %, at least 95 wt %, at least 98 wt %, or at least 99 wt %.

In another specific embodiment, during production of the composition comprising polyketal Ie, If, or Ig, the byproducts include diketocarboxylic ester IVa, hydroxy ketoester VIb, hydroxy ketal ester VIIb, or a combination comprising at least one of the foregoing compounds,

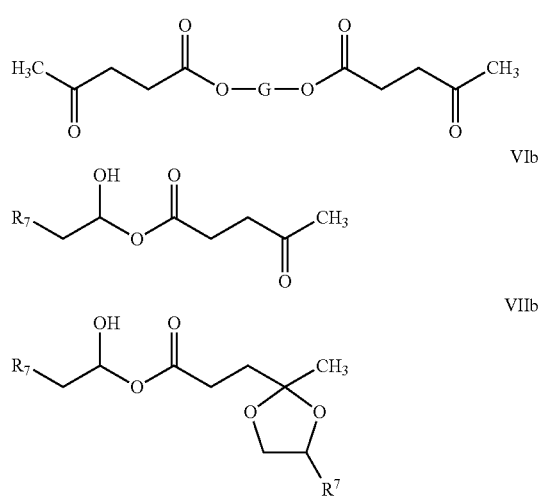

wherein G and $R^7$ is as defined in polyketal adduct Ie, If, and Ig. The hydroxy ketoester VIb and the hydroxy ketal ester VIIb can themselves each be isolated, in a purity of at least 80 wt %, at least 90 wt %, at least 95 wt %, at least 98 wt %, or at least 99 wt %.

In another specific embodiment, during production of the composition comprising polyketal Ih, Ii, or Ij, the byproducts include diketocarboxylic ester IVa, hydroxy ketoester VIc, hydroxy ketal ester VIIc, or a combination comprising at least one of the foregoing compounds,

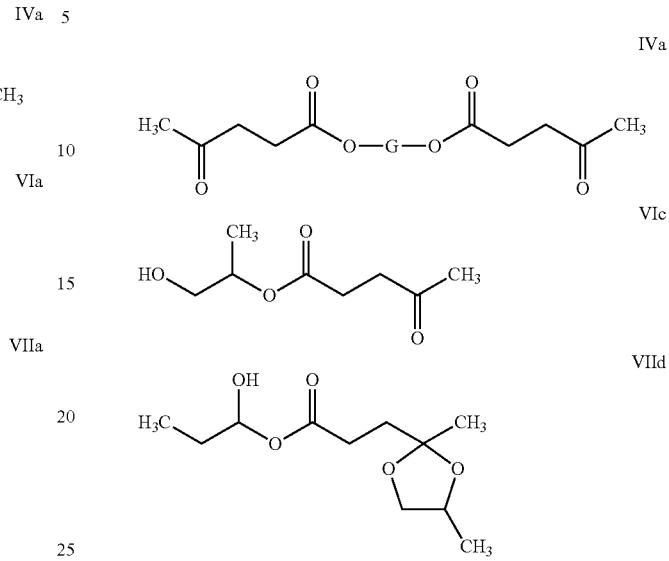

wherein G is as defined in polyketal Ih, Ii, or Ij. The hydroxy ketoester VIc and the hydroxy ketal ester VIIc can themselves each be isolated, in a purity of at least 80 wt %, at least 90 wt %, at least 95 wt %, at least 98 wt %, or at least 99 wt %.

In any of the foregoing embodiments, byproducts IV, VI, and VII can each be present in an individual amount of 0-10 wt %, up to 10 wt %, specifically 0.1 to 8 wt %, more specifically 0.5-5 wt %, based on the total weight of the polyketal adduct composition. In an embodiment, the total amount of byproducts IV, VI, and VII is 0-30 wt %, up to 30 wt %, specifically 0.3-24 wt %, more specifically 0.5-15 wt %, or 0.1 to 10 wt %, based on the total weight of the polyketal adduct composition.

In a specific embodiment, use of the foregoing processes can produce a composition comprising the polyketal adduct Ia, Ib, Ie, or Ih having a purity of 80% or more, 90% or more, 95% or more, 98% or more, or 99 or more. In other words, a composition comprising the polyketal adduct Ia, Ib, Ie, or Ih, contains at least 80 wt %, at least 90 wt %, or at least 95 wt %, at least 98 wt %, or at least 99 wt % of the polyketal adduct, based on the total weight of the composition, with the remainder being other components. The other components in this embodiment can include ketocarboxylic acid III, polyketocarboxylic ester IV, polyol V, hydroxy ketoester VI, a hydroxy ketal ester VII, sulfur compounds as discussed herein, a transition metal as discussed herein, an oligomer as discussed herein, and other specific polyketal adducts, specifically Ic, Id, If, Ig, Ii, and Ij, other reaction byproducts, and combinations comprising at least one of the foregoing.

The high purities of the polyketal adduct I with respect to sulfur, oligomer, and transition metals results in a number of advantageous properties. For example, the polyketal adduct I can have a low yellowness index (YI), for example a YI of less than or equal to about 200, specifically less than or equal to about 150, and more specifically less than or equal to about 100 as measured by ASTM E313. In a specific embodiment, the polyketal adduct I can have a YI of less than or equal to about 100, specifically less than or equal to about 50, and more specifically less than or equal to about 10 as measured by ASTM E313. In a particularly advantageous feature, such levels are obtainable without distillation of the polyketal adduct I after synthesis.

In a specific embodiment, the polyketal adduct Ia, Ib, Ie, is obtained in a purity of greater than 50 wt %, specifically greater than 70 wt %, more specifically greater than 80 wt %, or greater than 90 wt %. As used herein "purity" refers to the total composition, which can contain additional products such as diketocarboxylic ester IV, the partially ketalized ester VI, or the starting ketocarboxy compound III. Purity can be determined via GC-MS as described in the Examples below.

Of course, the polyketal adduct I can be further purified, for example by extraction or distillation. The distillation of the polyketal adduct I for can be carried out with wiped film evaporators, spinning film evaporators, rotary evaporators, falling film evaporators and other similar equipment. In embodiments, the polyketal adduct I can be removed to a small extent in the first distillation column and subsequently re-used by mixing with additional fresh reactants.

The polyketal adduct I can be used as an additive in a variety of organic polymers to form a polymer composition, for example as a plasticizer in a variety of organic polymers to form a plasticized polymer. The organic polymer can be a thermoplastic or a thermoset. In an exemplary embodiment, the polymer is a thermoplastic. Examples of the organic polymer are cellulosics, polyacetals, polyacrylics, polyamideimides, polyamides, polyanhydrides, polyarylates, polyarylsulfones, polybenzoxazoles, polycarbonates, polyesters, polyetherketones, polyethersulfones, polyether ether ketones, polyether ketone ketones, polyetherimides, polyimides, polylactic acids, polyolefins, polyphenylene sulfides, polyphosphazenes, polyphthalides, polysilazanes, polysiloxanes, polystyrenes, polysulfides, polysulfonamides, polysulfonates, polysulfones, polysulfones, polytetrafluoroethylene, polythioesters, polyureas, polyvinyl acetates, polyvinyl alcohols, polyvinyl chlorides, polyvinyl esters, polyvinyl ethers, polyvinyl halides, polyvinyl ketones, polyvinyl nitriles, polyvinyl thioethers, polyhydroxyalkanoates, or the like, or a combination comprising at least one of the foregoing organic polymers.

Specific examples of organic polymers that can be plasticized by the polyketal adduct I are poly(vinyl chloride), poly(vinylidene chloride), polyhydroxyalkanoates, poly(lactic acid), polystyrene, polycarbonate, polyurethanes or ureas, acrylic polymers, styrene-acrylic polymer, vinyl-acrylic polymers, ethylene-vinyl acetate polymers, polyesters, polyamides, polyethers, acrylonitrile-butadiene-styrene polymers, styrene-butadiene-styrene polymers, poly(vinyl acetate), poly(vinyl butyrate), poly(ethylene vinyl acetate) copolymers, polyketal esters and copolymer thereof, cellulosics, thermoplastic elastomers, or random, graft, or block copolymers thereof The polyketal adduct can be added to the organic polymer in amounts effective to perform the intended function of the polyketal adduct I, for example plasticizing. Generally, the polyketal adducts I are present in the polymer compositions in amounts of about 0.1 to about 90 wt %, specifically about 4 to about 70 wt %, and more specifically about 40 to about 60 wt %, based on the total weight of the organic polymer composition.

In an embodiment, in one method of manufacturing a polymer composition, specifically a plasticized polymer composition, the polyketal adduct I is combined, for example blended with an organic polymer. The blending generally involves melt blending. Melt blending comprises melting a thermoplastic polymer and dispersing the polyketal adduct I into the molten thermoplastic polymer. Pre-blending of the thermoplastic polymer and the polyketal adduct I can be conducted prior to the melt blending. For example, the compositions can be prepared by pre-blending the thermoplastic polymer and the polyketal adduct I prior to being fed into a melt-blending device. The pre-blending can be carried out in a mixer such as a drum mixer, ribbon mixer, vertical spiral mixer, Muller mixer, sigma mixer, chaotic mixer, static mixer, and the like. Pre-blending is generally carried out at room temperature. Pre-blending is not always desirable.

Melt blending involves the use of shear force, extensional force, compressive force, ultrasonic energy, electromagnetic energy, thermal energy or combinations comprising at least one of the foregoing forces or forms of energy, and is conducted in processing equipment wherein the aforementioned forces or forms of energy are exerted by a single screw, multiple screws, intermeshing co-rotating or counter rotating screws, non-intermeshing co-rotating or counter rotating screws, reciprocating screws, screws with pins, screws with screens, barrels with pins, rolls, rams, helical rotors, or combinations comprising at least one of the foregoing. Specifically, melt blending involving the aforementioned forces can be conducted in machines such as single or multiple screw extruders, Buss kneaders, Henschel mixers, helicones, Ross mixers, Banbury, roll mills, molding machines such as injection molding machines, vacuum forming machines, blow molding machines, or the like, or a combination comprising at least one of the foregoing machines.

After melt blending, an intermediate product such as pellets or briquettes can be formed, which can then be used for subsequent manufacture into an article, for example by molding. Alternatively, the melt-blended composition can be used in the direct formation of articles via casting to form a layer or molding into an article having a desired shape. Molding can be conducted by compression molding, injection molding, vacuum forming, extrusion, blow molding, or the like.

In a specific embodiment, the polyketal adducts I are used as a plasticizer, and in particular in a plastisol. As used herein, the term "plastisol" means a flowable suspension of polymer particles in a plasticized emulsion that forms a solid, flexible, plasticized polymer product with the addition of heat. When used to perform a plasticizing function, the polyketal adduct I can have viscosities less than about 500 centipoise (cP) at 25° C. The viscosity can be from about 1 cP to about 250 cP; specifically about 50 cP to about 200 cP at 25° C. Low viscosity provides for ease of compounding into one or more polymer compositions without, for example, preheating or addition of diluents or solvents to lower viscosity. Low viscosity and high solvating enables the creation of pastes such as plastisols.

In certain embodiments, at least a portion of the polyketal adduct I is in a liquid phase of the plastisol. A preferred polymer phase of the plastisol is (polyvinylchloride) although other polymer particles can be used. A plastisol can contain from 10 to 90 wt % of the polyketal adduct I. Polymer plastisols are poured into a mold or onto a surface where the subsequent addition of heat causes the suspension to form a solid, flexible mass. In such embodiments, it is important for the plasticizer to cause "fusing", which means that the polymer particle boundaries of the plastisol are broken by the effect of the plasticizer, causing mixing of the polymer on a molecular scale, wherein the effect persists to the solid state. The polyketal adduct I functions well as a "fast fusing plasticizer", which means that they shorten the time required for the polymer particle boundaries of the plastisol to be broken and mixing to occur, lower the temperature required for the polymer particle boundaries of the plastisol to be broken and mixing to occur, or both.

Plastisols are useful in the production of sheet stock or films, flooring, tents, tarpaulins, coated fabrics such as automobile upholstery, in car underbody coatings, in moldings and other consumer products. Plastisols are also used in medical uses such as blood bags and multilayered sheets and films, tubing, footwear, fabric coating, toys, flooring products and wallpaper.

Plastisols comprise about 40 to about 200 parts by weight, specifically about 50 to about 150 parts by weight, more specifically about 70 to about 120 parts by weight, and more specifically about 90 to about 110 parts by weight of plasticizer per 100 parts of dispersed polymer particles.

Polyvinylchloride plastisols can be made from polyvinylchloride that has been produced by emulsion polymerization. In an exemplary embodiment, the polyketal adduct I is present in a polyvinylchloride plastisol composition comprising about 40 to about 200 parts by weight, specifically about 50 to about 150 parts by weight, specifically about 70 to about 120 parts by weight, and more specifically about 90 to about 110 parts by weight of the polyketal adduct per 100 parts of polyvinylchloride. Such plastisol compositions tend to have stable viscosities; their viscosities tend to increase less than about 200% over a period of 14 days when stored at a temperature of about 20° C. to 25° C., or less than about 100%, specifically less than 70% and more specifically less than 50% when stored at a temperature of about 20° C. to 25° C. for five days.

A process for the production of flexible polyvinylchloride articles is also provided, whereby a layer is formed on a substrate from a plastisol containing about 40 to about 200 parts by weight, specifically about 50 to about 150 parts by weight, specifically about 70 to about 120 parts by weight, and more specifically about 90 to about 110 parts by weight of a plasticizer composition containing the polyketal adduct I per 100 parts by weight of polyvinylchloride, and subsequently fusing the layer to the substrate by the application of heat.

The polyketal adduct can also be used in conjunction with other plasticizers in an organic polymer. Examples of other plasticizers are dialkyl phthalates, trimethyl pentanyl diisobutyrate, dialkyl isophthalates, dialkyl terephthalates, alkyl benzyl phthalates, dialkyl adipates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, epoxidized soybean oil, acetylated castor oil, and mixtures thereof.

A variety of additives can be used with the polyketal adduct or in the polymer compositions, for example the plasticized polymer compositions. These additives can include an antioxidant, an antiozonant, a thermal stabilizer, a mold release agent, a dye, a pigment, an antibacterial, a flavorant, a fragrance molecule, an aroma compound, an alkalizing agent, a pH buffer, a conditioning agent, a chelant, a solvent, a surfactant, an emulsifying agent, a foam booster, a hydrotrope, a solubilizing agent, a suspending agents, a humectant, an accelerator, a ultraviolet light absorber, an antifouling agent, a flame retardant additive, an odor scavenging agent, a blowing agent, a processing aid, an impact modifier, a toughener, an adjuvant, a cross-linking agent, or a combination comprising at least one of the foregoing additives.

The polymer composition, in particular the plasticized polymer compositions are useful to form a variety of articles. An "article" as used herein is an item with a discrete shape, such as a tube, a film, a sheet, or a fiber, that incorporates one or more compositions of the disclosure; in some embodiments, the article can have its origin in a composition that undergoes a transformation, such as solidification or evaporation of one or more solvents, to result in the final article. In some embodiments, an article is substantially formed from a polymer composition of the invention; in other embodiments, the polymer composition of the invention forms only one part, such as one layer, of an article.

The article is, in some embodiments, a casing, a pipe, a cable, a wire sheathing, a fiber, a woven fabric, a nonwoven fabric, a film, a window profile, a floor covering, a wall base, an automotive item, a medical item, a toy, a packaging container, a screw closure or stopper adapted for a bottle, a gasket, a sealing compound, a film, a synthetic leather item, an adhesive tape backing, or an item of clothing. In some embodiments, the casing is a casing for an electrical device. In some embodiments, the medical item is medical tubing or a medical bag. In some embodiments, the film is a roofing film, a composite film, a film for laminated safety glass, or a packaging film. In some embodiments, the packaging container is a food or drink container. In some embodiments, the sealing compound is for sealed glazing. In some embodiments, the automotive item is seat upholstery, an instrument panel, an arm rest, a head support, a gear shift dust cover, a seat spline, a sound-deadening panel, a window seal, a landau top, a sealant, a truck tarpaulin, a door panel, a cover for a console and glove compartment, a trim laminating film, a floor mat, a wire insulation, a side body molding, an underbody coating, a grommet, or a gasket.

The polyketal adduct I can be used in a variety of personal care products such as shampoos, lotions, shaving creams, deodorants, and the like. In an embodiment, the polyketal adduct I can be converted into a polymer that is used as a plasticizer, a toughener, a surfactant, a barrier layer compound, an interfacial modifier, a compatibilizer, or a phase transfer compound.

The following examples, which are meant to be exemplary, not limiting, illustrate compositions and methods of manufacturing of some of the various embodiments described herein.

EXAMPLES

Example 1

Synthesis of levulinic acid-1,4-butanediol-levulinic acid (LA-BDO-LA) with sulfuric acid catalyst This example was conducted to demonstrate a reaction between a hydrocarbon polyol II and a ketocarboxy compound III to isolate the polyketocarboxylic ester IV. The reaction is shown in Scheme 1.

Scheme 1

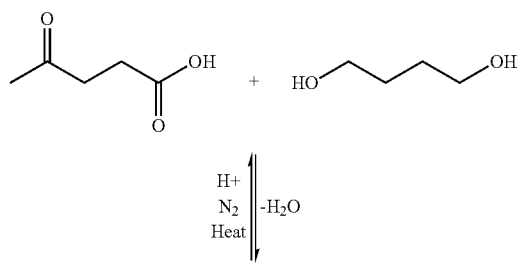

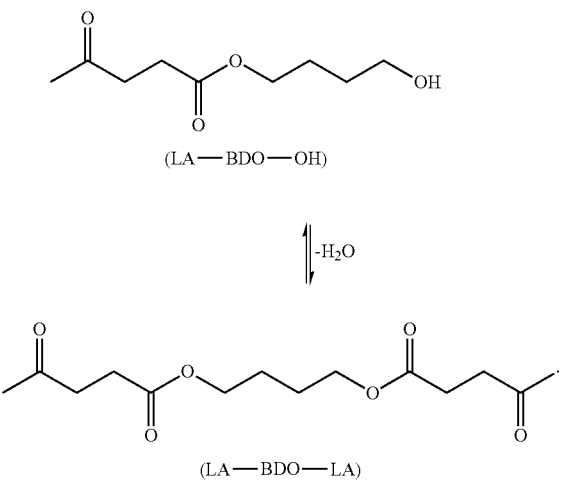

(LA—BDO—OH)

↓ -H₂O (LA—BDO—LA)

Levulinic acid (268.7 g, 2.3 mol), 1,4-butanediol (100.4 g, 1.1 mol), and sulfuric acid (99.8 µL, 500 ppm) were added to an empty 500 mL, 3-neck round bottom flask equipped with a magnetic stir-bar, Dean-Stark trap and overhead condenser, a thermocouple, and a nitrogen inlet. The contents were heated with a heating mantle for 2 hours from 140-180° C. The reaction began to produce a volatile condensate at 140° C. As the reaction progressed over time, the temperature was increased incrementally in order to increase the rate of volatile condensate. The maximum temperature of the reaction was 180° C. Volatile condensate was collected in the Dean Stark trap.

A sample of the condensate was evaluated for the presence of tetrahydrofuran (THF). The condensate was measured to contain 20 wt % tetrahydrofuran, which correlates to greater than 10% yield loss (conversion) of 1,4-butanediol to tetrahydrofuran during the esterification reaction.

A sample of the reactor was analyzed by gas chromatography-flame ion detection (GC-FID) and the composition was found to be:

| | |
|---|---|
| 0.09% | un-reacted 1,4-butanediol, |
| 10.2% | un-reacted levulinic acid, |
| 1.3% | of hydroxy capped polyketocarboxylic ester (LA-BDO-OH), |
| 78% | of diketocarboxylic ester (LA-BDO-LA) product, and |
| 8.4% | unknown higher molecular weight species. |

Based on the un-reacted levulinic acid in the final composition, the formation of unknown higher molecular weight compounds, and the formation of a considerable amount of tetrahydrofuran, this process was found to be less selective toward the synthesis of LA-BDO-LA product.

Example 2

Synthesis of diketocarboxylic ester (LA-BDO-LA) with camphor sulfonic acid catalyst As illustrated in Scheme 1, levulinic acid (268.3 g, 2.3 mol), 1,4-butanediol (99.3 g, 1.1 mol), and camphor sulfonic acid (75.1 mg, 200 ppm) were added to an empty 500 mL, 3-neck round bottom flask equipped with a magnetic stir-bar, Dean-Stark trap and overhead condenser, a thermocouple, and a nitrogen inlet. The contents were heated with a heating mantle for 6 hours at 140-180° C. The reaction began to produce volatile condensate at 140° C. As the reaction progressed over time, the temperature was increased incrementally in order to increase the rate of volatile condensate. The maximum temperature of the reaction was 180° C. Volatile condensate was collected in the Dean Stark trap.

A sample of the condensate was evaluated for the presence of tetrahydrofuran (THF). The condensate was measured to contain 1.8 wt % tetrahydrofuran, which correlates to less than 1% yield loss of 1,4-butanediol to tetrahydrofuran during the esterification reaction.

A sample of the reactor was analyzed by GC-FID and the composition was found to be as follows.

| | |
|---|---|
| 0.10%: | un-reacted 1,4-BDO |
| 10.6%: | un-reacted levulinic acid |
| 8.8%: | hydroxy capped polyketocarboxylic ester (LA-BDO-OH) |
| 78%: | diketocarboxylic ester (LA-BDO-LA) product |
| 1.7%: | unknown higher molecular weight species |

Based on the absence of a significant amount of unknown higher molecular weight compounds and the low yield loss of 1,4-butanediol to tetrahydrofuran, this process was found to be selective for the synthesis of LA-BDO-LA in high yields. This product crystallized after cooling. The crude brownish crystals were washed once with deionized water, and the product was filtered and dried into an off-white crystalline product. The yield of product was 200 grams. The composition by GC-FID was found to be as follows:

| | |
|---|---|
| 0.13%: | un-reacted 1,4-BDO |
| 0.65%: | un-reacted levulinic acid |
| 1.1%: | hydroxy capped polyketocarboxylic ester (LA-BDO-OH) |
| 97.8%: | diketocarboxylic ester (LA-BDO-LA) product |
| 0.2%: | unknown higher molecular weight species |

Example 3

Recrystallization of LA-BDO-LA

The LA-BDO-LA product from Example 2 was recrystallized in water to form white, shiny, spherical flakes and needle-shaped crystals. The crystalline sample was dried and analyzed using GC-FID. The crystalline sample had the following composition.

| | |
|---|---|
| non-detectable: | 1,4-BDO |
| 0.2%: | Un-reacted levulinic acid |
| 0.2% | LA-BDO-OH |
| 99.4% | LA-BDO-LA product |
| 0.1% | unknown higher molecular weight species |

Comparing examples 2 and 3, it can be seen that crystallizing the diketocarboxylic ester improves the purity of the diketocarboxylic ester to greater than 99%. Examples 4-13. The following examples were performed according to the general procedures in Examples 1-2. The temperatures, catalysts, and time of reaction were varied to obtain high conversion without sacrificing selectivity to product (THF formation). All reactions were conducted under a nitrogen purge. The results are shown in the Table 1.

TABLE 1

| Ex. | moles LA | moles BDO | ppm Catalyst | T (°C.) | N₂/Vac (Torr) | Time (h) | Conversion by % LA Consumption | % LA-BDO-LA Yield | % THF in Overheads | % Higher MW |
|---|---|---|---|---|---|---|---|---|---|---|
| 4 | 2.1 | 1 | 50 Camphor sulfonic acid | 180 | N₂ | 6.5 | 86.19 | 83 | 2.6 | 1.6 |
| 5 | 2.1 | 1 | 10000 Amberlyst ® 35 | 130 | N₂ | 5 | 47.17 | 52 | 49.9 | 1.0 |
| 6 | 2.1 | 1 | 10000 Amberlyst ® 35 | 110 | N₂ | 5 | 56.32 | 28 | 1.6 | 0.4 |
| 7 | 2.1 | 1 | 10000 Amberlyst ® 35 | 130 | 20 | 5.5 | 61.60 | 46 | 1.7 | 9.0 |
| 8 | 2 | 1 | 200 Camphor sulfonic acid | 160 | N₂ | 21.5 | 92.97 | 86 | 5.8 | 2.2 |
| 9 | 2 | 1 | 500 Tin II octanoate | 160 | N₂ | 24 | 94.97 | 83 | 0.6 | 1.9 |
| 10 | 2.1 | 1 | 0 | 150 | N₂ | 8.5 | 85.15 | 73 | 0.45 | 4.5 |
| 11 | 2 | 1 | 1000 Nafion ® Sac 13 | 150-205 (ramp) | N₂ | 19.0 | 99.4 | 70 | 5.13 | 4.4 |
| 12 | 2 | 1 | 200 ppm Ti(OiPr)₄ | 160 | N₂ | 24 | 97.71 | 81 | 2.2 | 5.4 |
| 13 | 2 | 1 | 200 Camphor sulfonic acid | 150 (2 h); 210 (12 h) | N₂ | 12 | 97 | 82 | not meas. | 3.8 |

A variety of different catalysts and reaction conditions were used to make the di-levulinic ester, LA-BDO-LA. Example 5 showed that due to the presence of a higher amount of heterogeneous acid catalyst, a loss of selectivity was noticed due to high THF formation. However, upon using less heterogeneous catalyst in Examples 6-7, the catalyst was more selective without sacrificing the reaction conversion. The reactions showed a yield of greater than 80% and greater than 95% selectivity for most cases.

Example 14

Synthesis of Ketalized LPK-BDO-LPK

This example was conducted to demonstrate the manufacturing of the polyketal adduct I from the LA-BDO-LA synthesized in the Example 2 by reacting the diketocarboxylic ester (LA-BDO-LA) with the polyol V. LA-BDO-LA is reacted with 1,2-propane diol to manufacture the polyketal adduct I as shown in the Scheme 2.

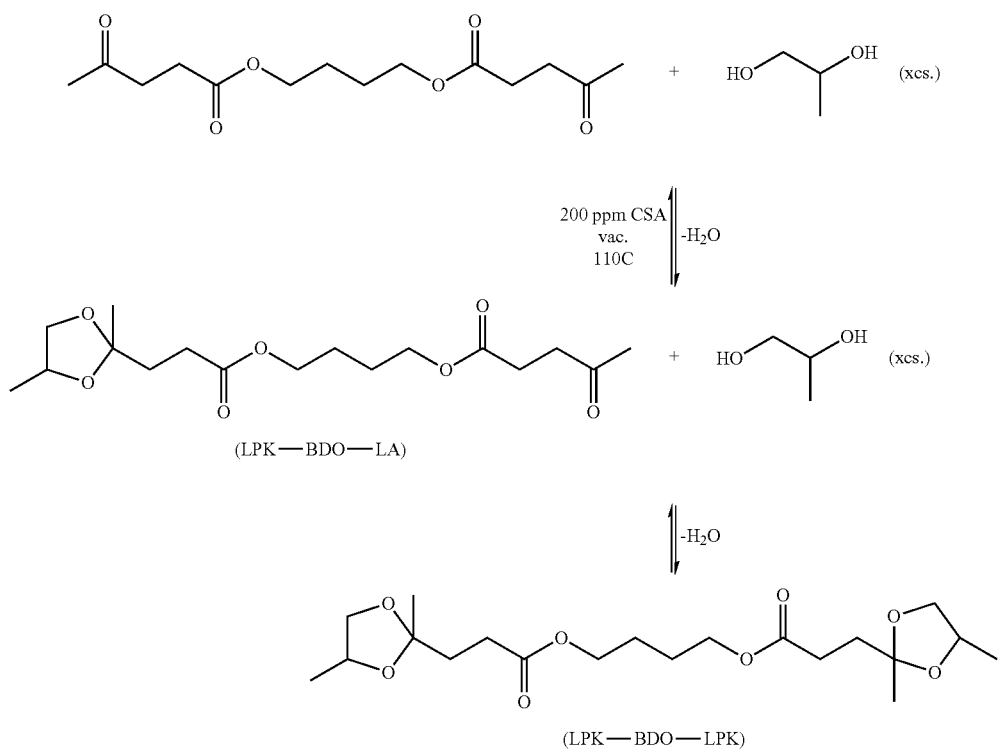

The LA-BDO-LA product from Example 2 (57.3 g, 0.2 mol), 1,2-propane-diol (60.8 g, 0.8 mol), and camphor sulfonic acid (24 mg, 200 ppm) were added to an empty 250 mL, 3-neck round bottom flask equipped with a magnetic stir-bar, Dean-Stark trap and overhead condenser, a thermocouple, and a glass stopper. The contents were heated with a heating mantle for 1 hour at 110° C. under a vacuum of 30 Torr. Volatile condensate was collected in the Dean Stark trap.

After 1 hour, a sample was removed from the reactor and analyzed by GC-FID. The composition was found to be:

| | |
|---|---|
| 8% | 1,2-propane diol |
| 0.09% | un-reacted LA-BDO-LA |
| 5.9% | LPK-BDO-LA |
| 79.5% | LPK-BDO-LPK product |
| 6% | other products |

The reaction was cooled and neutralized with solid dibasic sodium phosphate. The reaction mixture was filtered, and the excess 1,2-propane diol was removed by vacuum distillation. The composition of the final product by GC-FID was found to be:

| | |
|---|---|
| non-detectable: | levulinic acid or 1,4-BDO |
| 0.4% | 1,2-propane diol |
| 0.15% | un-reacted LA-BDO-LA |
| 7.6% | LPK-BDO-LA |
| 85% | LPK-BDO-LPK product |
| 6.8% | other products. |

The product was a dark yellow liquid, YI=98. This sample was analyzed by GPC and it was found that it did not contain any higher molecular weight oligomers. This compares favorably with other methods of manufacturing the polyketal adduct I where high molecular weight oligomers are produced.

Example 15

Synthesis of LPK-BDO-LPK

The LA-BDO-LA product of Example 3 (28.6 g, 0.1 mol), 1,2-propane-diol (30.4 g, 0.4 mol), and AMBERLYST® 35 cationic exchange resin (0.59 g, 1%) were added to an empty 250 mL, 3-neck round bottom flask equipped with a magnetic stir-bar, Dean-Stark trap and overhead condenser, a thermocouple, and a glass stopper. The contents were heated with a heating mantle for 1 hour at 110° C. under 30 Torr vacuum. Volatile condensate was collected in the Dean Stark trap.

After 1 hour, a sample was removed from the reactor and analyzed by GC-FID. The composition was found to be:

| | |
|---|---|
| 8.5% | 1,2-propane diol |
| 0.2% | un-reacted LA-BDO-LA |
| 8.4% | LPK-BDO-LA |
| 78.6% | LPK-BDO-LPK product |
| 4.3% | other products. |

The excess 1,2-propane diol was removed by vacuum distillation. The product was a very slightly yellow liquid (YI<5). This sample was analyzed by gel permeation chromatography (GPC) and it was found that it did not contain any high molecular weight oligomers. This compares favorably with other methods of manufacturing the polyketal adduct I where high molecular weight oligomers are produced. In a particularly advantageous feature, the polyketal adduct I is apparently a novel composition obtained free of higher molecular weight oligomers.

From the results obtained in examples, it can be seen that camphor sulfonic acid provides better yields of the diketocarboxylic ester especially when compared to sulfuric acid. The camphor sulfonic acid is therefore a more selective catalyst for manufacturing the diketocarboxylic ester.

In addition, it can be seen that washing of the diketocarboxylic ester crystals with water produces purer diketocarboxylic ester. The synthesis of the polyketal adduct from the purer diketocarboxylic ester obtained from the Examples 2 and 3 also does not produce any undesirable high molecular weight species. In addition, the polyketal adduct I has a yellowness index of less than or equal to about 200, specifically less than or equal to about 150, and more specifically less than or equal to about 100 as measured by ASTM E313.

From the results obtained in this example, it can be seen that recrystallization of the crystals, from both the aqueous phase and the organic phase, results in an increased LA-BDO-LA purity from 99.0% to 99.7% and greater. More specifically, the recrystallized crystals from the aqueous phase resulted in 99.9% LA-BDO-LA purity with no levulinic acid detected and the recrystallized crystals from the organic phase, after washing with water and sodium bicarbonate, resulted in 99.8% LA-BDO-LA purity.

Examples 16-21

The Following Examples were Performed to Study the Effect of the Ratio of LA-BDO-LA/Levulinic Acid and Temperature on Crystallization Yield and Purity In the following examples, the purified LA-BDO-LA was 99.6% pure and washed with sodium bicarbonate and the purified levulinic acid was recrystallized from a hexane/ethyl acetate mixture.

Example 16

Crystallization of LA-BDO-LA Intermediate

A reaction mixture of 4:1 levulinic acid:1,4-butanediol were esterified in a 5 gallon Parr reactor to yield a yellow, product mixture of 60% LA-BDO-LA and 40% levulinic acid. The product mixture was allowed to partially crystallize at room temperature to result in clear crystals. The crystalline sample had the following composition as identified by GC-FID. The composition was found to be:

| | |
|---|---|
| 98-99%: | LA-BDO-LA product |
| 1%: | un-reacted levulinic acid |

The yellow liquid had the following composition as identified by GC-FID. The composition was found to be:

| | |
|---|---|
| 37%: | LA-BDO-LA product |
| 61%: | un-reacted levulinic acid |
| 1%: | LA-BDO-OH |
| 1%: | other. |

Examples 17-21

The Effect of the Ratio of LA-BDO-LA to Levulinic Acid in the Product Mixture on Crystallization Yield The effect of the ratio of LA-BDO-LA to levulinic acid was determined by adding either purified LA-BDO-LA or purified levulinic acid to the product mixture of Example 16 in 20 mL scintillation vials. The samples were heated and agitated until homogeneous. Specifically, 5 and 2 g of purified LA-BDO-LA were added in Examples 17 and 18, respectively, and 2 and 5 g of purified levulinic acid were added in Examples 20 and 21, respectively. Neither purified LA-BDO-LA nor purified levulinic acid was added in Example 19. The samples were stored at room temperature (17-18° C.) and agitated by hand daily for up to 7 days or until crystallization was observed. Following crystallization, samples were separated into solid and liquid by filtration through a fritted funnel. The vial was rinsed with cold deionized water and poured through the same funnel. The crystals were collected and dried via vacuum pump or were allowed to dry on a watch glass at room temperature. The results are shown in Tables 2 and 3.

TABLE 2

|  | Example | |
| --- | --- | --- |
|  | 17 | 18 |
| Product Mixture (g) | 10 | 10 |
| Purified LA-BDO-LA (g) | 5 | 2 |
| Purified levulinic acid (g) | 0 | 0 |
| % LA-BDO-LA/% levulinic acid | 73/27 | 67/33 |
| Phase | Solid, little liquid | Solid, little liquid |

Examples 17 and 18, show that samples with greater than about 60% LA-BDO-LA crystallized nearly entirely such that separation from the liquid phase was made difficult if not impossible due to entrapment of liquid within the crystal.

TABLE 3

|  | Example | | |
| --- | --- | --- | --- |
|  | 19 | 20 | 21 |
| Product Mixture (g) | 10 | 10 | 10 |
| Purified LA-BDO-LA (g) | 0 | 0 | 0 |
| Purified levulinic acid (g) | 0 | 2 | 5 |
| % LA-BDO-LA/% levulinic acid | 59/41 | 50/50 | 40/60 |
| Crystal Produced (g) | 3.69 | 2.63 | 0.53 |
| LA-BDO-LA (%) | 96.7 | 93.5 | 98.0 |
| levulinic acid (%) | 3.1 | 6.3 | 1.9 |
| LA-BDO-OH (%) | 0.1 | 0.1 | — |
| Other (%) | 0.1 | 0.1 | 0.1 |
| Mother Liquor (g) | 5.40 | 7.99 | 14.03 |
| LA-BDO-LA (%) | 35.4 | 36.0 | 38.3 |
| levulinic acid (%) | 62.8 | 62.8 | 60.9 |
| LA-BDO-OH (%) | 1.0 | 0.9 | 0.6 |
| Other (%) | 0.8 | 0.3 | 0.2 |

From the results obtained in Examples 19-21 a clear trend can be seen towards increasing crystal yield as the LA-BDO-LA/levulinic acid ratio increases. Since the total mass of material used in each sample is different, yield can be adjusted for this factor by dividing crystal mass over total LA-BDO-LA mass in the starting mixture. 3.69 g/5.8 g=63.6% for Example 19 (60/40), 2.63 g/6 g=43.8% for Example 20 (50/50), and 0.53 g/6 g=8.8% for Example 21 (40/60). GC-FID analysis of the mother liquor shows it retaining between 35-38% LA-BDO-LA while crystal purity ranges from 93-98% LA-BDO-LA.

Examples 22-24

The Effect of the Ratio of LA-BDO-LA to Levulinic Acid in Purified Mixtures on Crystallization Yield Purified LA-BDO-LA and purified levulinic acid were combined in ratios 60/40, 50/50, and 40/60 LA-BDO-LA/levulinic acid in Examples 22, 23, and 24, respectively, in 20 mL vials, heated and agitated by hand until homogeneous. The samples were stored at room temperature (17-18° C.) and agitated by hand daily for up to 7 days or until crystallization was observed. Following crystallization, samples were separated into solid and liquid by filtration through a fitted funnel. The vial was rinsed with cold deionized water and poured through the same funnel. The crystals were collected and dried via vacuum pump or were allowed to dry on a watch glass at room temperature. The results are shown in Table 4.

TABLE 4

|  | Example | | |
| --- | --- | --- | --- |
|  | 22 | 23 | 24 |
| Purified LA-BDO-LA (g) | 6 | 5 | 4 |
| Purified levulinic acid (g) | 4 | 5 | 6 |
| % LA-BDO-LA/% levulinic acid | 60/40 | 50/50 | 40/60 |
| Crystal Produced (g) | 4.17 | 2.45 | 0.95 |
| LA-BDO-LA (%) | 98.3 | 96.8 | 98.1 |
| levulinic acid (%) | 1.6 | 3.1 | 1.8 |
| Other (%) | 0.1 | 0.1 | 0.1 |
| Mother Liquor (g) | 4.91 | 6.07 | 8.20 |
| LA-BDO-LA (%) | 37.9 | 38.6 | 38.8 |
| levulinic acid (%) | 61.5 | 61.1 | 61.0 |
| LA-BDO-OH (%) | 0.3 | 0.2 | 0.1 |
| Other (%) | 0.3 | 0.1 | 0.1 |

As was shown in the previous examples, the 60/40, 50/50, and 40/60 LA-BDO-LA/levulinic acid pure mixtures also show a clear trend towards increasing crystal yield as the LA-BDO-LA/levulinic acid ratio increases. The same correction factor used in the crude mixtures of differing total masses is probably not needed for comparison but provided anyway. Yields for crystallization are calculated as a percentage of crystal mass recovered from the total LA-BDO-LA mass in the starting mixture. 4.17 g/6.0 g=69.5% for Example 22 (60/40), 2.45 g/5.0 g=49.0% for Example 23 (50/50), and 0.95 g/4.0 g=23.8% for Example 24 (40/60). GC-FID analysis of the mother liquor shows it retaining between 37-38% LA-BDO-LA while the crystal purity ranges from 96-98%.

Examples 25-26

The Effect of Crystallization Temperature of LA-BDO-LA to Levulinic Acid in Purified Mixtures on Crystallization Yield Examples 25 and 26 were mixtures of purified LA-BDO-LA and purified levulinic acid combined in a 60/40 ratio in 20 mL vials, heated in separate oil baths at 30° C. and 40° C., respectively, for 20 days. Example 25 crystallized. Following crystallization, Example 25 was separated into solid or liquid by filtration through a fritted funnel. The vial was rinsed with cold deionized water and poured through the same funnel. The crystals were collected and dried via vacuum pump or were allowed to dry on a watch glass at room temperature. Example 26 did not crystallize and remained entirely liquid, even with agitation and seeding with LA-BDO-LA crystals. The results are shown in Table 5.

TABLE 5

|  | Example | |
| --- | --- | --- |
|  | 25 | 26 |
| Purified LA-BDO-LA (g) | 6 | 6 |
| Purified levulinic acid (g) | 4 | 4 |
| % LA-BDO-LA/% levulinic acid | 60/40 | 60/40 |
| Temperature (° C.) | 30 | 40 |
| Crystal Produced (g) | 1.93 | 0 |
| LA-BDO-LA (%) | 98.2 | — |
| levulinic acid (%) | 1.6 | — |
| LA-BDO-OH | 0.1 | — |
| Other (%) | 0.1 | — |
| Mother Liquor (g) | 8.17 | 10 |
| LA-BDO-LA (%) | 70.6 | ~60 |
| levulinic acid (%) | 28.8 | ~40 |
| LA-BDO-OH (%) | 0.4 | — |
| Other (%) | 0.2 | — |

Example 25 shows that lower temperatures provide for a higher recovery of LA-BDO-LA in the 60/40 LA-BDO-LA/levulinic acid system since Example 26 did not crystallize. Yields for crystallization can be calculated as described previously. 1.93 g/6.0 g=32.2% for Example 25. Crystal yield at 30° C. is about one half the 60/40 mixtures allowed to crystallize at 17-18° C. (63-70%). GC-FID analysis of the mother liquor shows it retaining 70% LA-BDO-LA while the crystal purity is 98%.

Examples 16-26 show that the recovery of LA-BDO-LA crystals occurs more readily and at a higher yield when either the ratio of LA-BDO-LA:levulinic acid is increased or the temperature is decreased, although decreasing temperature or increasing the LA-BDO-LA:levulinic acid ratio too far will lead to a decrease in separation of LA-BDO-LA and levulinic acid. Other separation techniques would help to optimize this process, such as a centrifuge or suspension crystallization in that levulinic acid entrapment within the crystals can be minimized or eliminated and washed away from the crystal.

Examples 27-30

The following examples were performed to study the effect excess water on crystallization yield and purity.

Example 27

Crystallization of LA-BDO-LA Crystals-Bench Scale

A large excess of water, specifically 384.6 g, was added to a 4:1 levulinic acid:LA-BDO-LA initial product mixture consisting of LA-BDO-LA, Levulinic Acid, and LA-BDO-OH and was allowed to crystallize. The results are shown in Table 6.

TABLE 6

|  | Initial Mixture | Crystals |
| --- | --- | --- |
| Water (g) | 384.6 | — |
| Mass (g) | 234.8 | 108.6 |
| LA-BDO-LA (%) | 60.5 | 99.2 |
| levulinic acid (%) | 37.8 | 0 |
| Other (%) | 1.7 | 0.8 |
| Yield (%) | — | 76.5 |

Recrystallization resulted in 108.6 g of LA-BDO-LA crystals of high purity, i.e. greater than 99%, and a high yield of 76.5%. Compared to Example 16, whose LA-BDO-LA purity in the resulting crystals was 98-99%, it can be seen from the results of Example 27 that large amounts of excess water results in an increase in LA-BDO-LA purity in the resulting crystals of greater than 99%.

Example 28

Crystallization of LA-BDO-LA Crystals-Large Scale

The conditions of Example 27 were repeated on a larger scale, except with a slightly lower excess of water due to volume constraints. The results are shown in Table 7.

TABLE 7

|  | Initial Mixture | $1^{st}$ Crystals | $2^{nd}$ Crystals |
| --- | --- | --- | --- |
| Water (g) | 4768.6 | — | — |
| Mass (g) | 3274.2 | 1274.2 | 217.1 |
| LA-BDO-LA (%) | 58.3 | 99.5 | 99.1 |
| levulinic acid (%) | 41.0 | 0.4 | 0.5 |
| LA-BDO-OH (%) | 0.7 | — | 0.1 |
| Other (%) | — | 0.1 | 0.3 |
| Yield (%) | — | 66.8 | 78.0 |

Example 28 resulted in 66.8% yield in the first crystal crop and eventually 78% when including the second crystal crop. Crystals contained slightly more levulinic acid than in the small-scale experiment above, but also produce crystals of high LA-BDO-LA purity of greater than 99%.

Example 29

Recrystallization of LA-BDO-LA Crystals by Re-Dissolving in Water

A small portion of crystals previously purified to 99+% was combined with water and heated until crystals melted. Two phases, aqueous on top, organic on bottom, were observed and separated. After 12 hours at room temperature, the aqueous layer yielded 15.5 g of crystals (washed with cold water) of 99.9% purity with no detectable levulinic acid. The organic layer was washed with cold water and yielded an estimated 135 g of crystals of high purity and low levulinic acid. These crystals were melted and washed with water again and the molten organic layer sampled to give high purity LA-BDO-LA with a low level of angelica lactone (0.007%). To this aqueous/organic mixture 35.5 g of saturated sodium bicarbonate was added, mixed well, and separated into organic and aqueous layers to give an estimated 115 g of LA-BDO-LA with no detectable levulinic acid. The results are shown in Table 8.

TABLE 8

|  | Initial Crystals | $1^{st}$ Crystals (Aqueous) | Crystals (Organic Layer) | Organic Layer (Water) | Organic Layer (NaHCO$_3$) |
| --- | --- | --- | --- | --- | --- |
| Water (g) | 287.7 | — | — | 292.4 | — |
| NaHCO$_3$ (g) | — | — | — | — | 35.5 |
| Mass (g) | 156.1 | 15.5 | ~135 | — | ~115 |
| LA-BDO-LA (%) | 99.0 | 99.9 | 99.7 | 99.8 | 99.8 |
| levulinic acid (%) | 0.5 | 0 | 0.2 | 0 | 0 |
| LA-BDO-OH (%) | 0.5 | 0.1 | 0.1 | 0.1 | 0.2 |
| Other (%) | — | — | — | 0.1 | — |
| Yield (%) | — | 9.9 | — | — | — |

From the results obtained in this example, it can be seen that recrystallization of the crystals, from both the aqueous phase and the organic phase, results in an increased LA-BDO-LA purity from 99.0% to 99.7% and greater. More specifically, the recrystallized crystals from the aqueous phase resulted in 99.9% LA-BDO-LA purity with no levulinic acid detected and the recrystallized crystals from the organic phase, after washing with water and sodium bicarbonate, resulted in 99.8% LA-BDO-LA purity.

Example 30

Recrystallization of LA-BDO-LA Crystals from a Reaction Mixture by Re-Dissolving in Water and Further Washing with Sodium Bicarbonate Example 30 recrystallizes a partially crystallized reaction mixture consisting of a mother liquor and crystals. The initial mixture weighed 1039.5 g and comprised 58.3% LA-BDO-LA and 41.0% levulinic acid. After approximately 24 hours, the yellow mother liquor was decanted and found to be composed of mostly levulinic acid. The remaining crystals, weighing 431.9 g, were washed and found to comprise 98.6% LA-BDO-LA and 1.2% levulinic acid. The crystals were then melted and combined with water. Poor separation was observed until saturated sodium chloride was added. The organic layer was separated to give a mixture of 90.1% LA-BDO-LA and 9.4% levulinic acid. This molten mixture was washed with water to yield a higher purity of LA-BDO-LA of 95.7% and 3.9% levulinic acid. A liquid portion was still visible long after the organic layer had crystallized was determined to be mostly levulinic acid, comprising 57.6% levulinic acid. The results are shown in Table 9.

TABLE 9

|  | Initial Mixture | Decanted Mother Liquor | Crystals | Organic Layer + NaCl | Crystallized Organic Layer | Liquid Removed |
|---|---|---|---|---|---|---|
| Water (g) | — | — | — | 229.7 | 275 | — |
| NaCl (g) | — | — | — | 104 | — | — |
| Mass (g) | 1039.5 | 607.6 | 431.9 | 457.4 | 412.3 | 45.1 |
| LA-BDO-LA (%) | 58.3 | 37.1 | 98.6 | 90.1 | 95.7 | 39.6 |
| levulinic acid (%) | 41.0 | 60.7 | 1.2 | 9.4 | 3.9 | 57.6 |
| LA-BDO-OH (%) | 0.7 | 1.2 | — | 0.3 | 0.2 | 2.1 |
| Other (%) | — | 1.0 | 0.2 | 0.2 | 0.2 | 0.7 |

The crystals from the crystallized organic layer were melted and washed with water to give crystals of similar purity. These crystals were then washed with saturated sodium bicarbonate solution to give a substantial reduction in levulinic acid content (0.6%). These crystals were washed again with saturated sodium bicarbonate to yield LA-BDO-LA with no detectable levulinic acid. The results are shown in Table 10.

TABLE 10

|  | Water Wash | NaHCO$_3$ Wash-1 | NaHCO$_3$ Wash-2 |
|---|---|---|---|
| NaHCO$_3$ (g) | — | 117.7 | 173.6 |
| Mass (g) | 407.1 | 347.4 | 350.5 |
| LA-BDO-LA (%) | 95.2 | 99.0 | 99.6 |
| levulinic acid (%) | 4.5 | 0.6 | — |
| LA-BDO-OH (%) | 0.2 | 0.3 | 0.3 |
| Other (%) | 0.1 | 0.1 | 0.1 |

From the results obtained in this example, it can be seen that recrystallization of the crystals and washing the crystals with saturated sodium bicarbonate results in an increased LA-BDO-LA purity of 99.0% and greater and little to no detectable amounts of levulinic acid.

Examples 31-38

The Effect of the Reaction Conditions Synthesis of LPK-BDO-LPK

LA-BDO-LA crystals of 99+% purity, Amberlyst A35 catalyst beads, and propylene glycol were added to a round bottom flask equipped with mechanical stirrer, thermocouple, and Dean-Stark/condenser. The flask was heated in an oil bath set to 110° C. and pressure reduced at varying rates. Following accumulation of a large excess of volatiles in the Dean-Stark trap, the reaction mixture was filtered through a 0.45 µm membrane and transferred to a single neck flask equipped with stir bar, Teflon boiling chips, and short-path distillation head. This flask was heated in a 110° C. in an oil bath and the pressure was reduced to less than 1 torr until boiling and volatilization was no longer observed. The resulting mixture was then analyzed for mass, content by GC/FID, yield, color, and thermal stability (as % mass loss at 115° C.). The conditions and results are shown in Table 11.

TABLE 11

|  | Example | | | | | | | |
|---|---|---|---|---|---|---|---|---|
|  | 31 | 32 | 33 | 34 | 35 | 36 | 37 | 38 |
| Time (min) | 115 | 190 | 380 | 105 | 120 | 35 | 70 | 120 |
| Reaction Temp. (° C.) | 110 | 107-115 | 109-128 | 113-125 | 75-117 | 83-93 | 57-90 | 70-98 |
| Vacuum (torr) | 150-39 | 150-53 | 60 | 60 | 200-36 | 75-6 | 26-13 | 30-13 |
| LPK-BDO-LPK (%) | 89.0 | 67.5 | 90.0 | 90.6 | 95.4 | 51.8 | 81.7 | 84.2 |
| Yield (mass %) | 89.5 | 92.5 | 74.5 | 94.0 | 95.2 | 83.2 | 91.2 | 94.8 |
| YI | 3.69 | 6.38 | ~30 | ~5 | ~1 | ~5 | ~5 | ~5 |
| Thermal Stability | | | | | | | | |
| Time (Days) | 7 | 10 | 7 | — | 7 | — | — | — |
| Stability (%) | 2.4 | 2.8 | 2.8 | — | 1.0 | — | — | — |

Amberlyst A35 catalyst beads (1.05 wt % based on the total reagent weight) were added in Examples 31 and 32 and dry Amberlyst A35 catalyst beads were added in Example 37. Example 33 was a large-scale example that initially resulted in only a 73% LPK-BDO-LPK purity following the PG stripping step. A WFE purification step was the performed in Example 33 to achieve 90% purity. Example 36 resulted in the lowest LPK-BDO-LPK conversion resulting in only 51.8% LPK-BDO-LPK, a longer reaction time was needed. In Example 38, the stir speed was reduced until the crystals melted, resulting in less Amberlyst A35 disintegration. Examples 31, 33-35, and 37-38 resulted in high purity LPK-BDO-LPK product of greater than 80%, of which Examples 33-35 resulted in purities of greater than 90%. Example 31-32, 34-35, and 37-38 resulted in high yields of greater than 89%. Examples 31 and 34-35 resulted in crystals of both high yield and high purity.

As used herein, the singular forms "a," "an," and "the" are intended to include the plural forms as well, unless the context clearly indicates otherwise. "Or" means "and/or." The endpoints of all ranges directed to the same component or property are inclusive of the endpoint and independently combinable, except when the modifier "between" is used. The modifier "about" used in connection with a quantity is inclusive of the stated value and has the meaning dictated by the context (e.g., includes the degree of error associated with measurement of the particular quantity). A "combination" is inclusive of blends, mixtures, alloys, reaction products, and the like.

In general, the compositions or methods can alternatively comprise, consist of, or consist essentially of, any appropriate components or steps disclosed. The invention can additionally, or alternatively, be formulated so as to be devoid, or substantially free, of any components, materials, ingredients, adjuvants, or species, or steps used in the prior art compositions or that are otherwise not necessary to the achievement of the function and/or objectives of the present claims.

Unless otherwise defined, all terms (including technical and scientific terms) used have the same meaning as commonly understood by one of ordinary skill in the art to which this invention belongs. Compounds are described using standard nomenclature. Any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. "Alkyl" means a straight or branched chain saturated aliphatic hydrocarbon having the specified number of carbon atoms. "Alkylene" means a straight or branched divalent aliphatic hydrocarbon group having the specified number of carbon atoms. "Aryl" means a cyclic moiety in which all ring members are carbon and a ring is aromatic. More than one ring can be present, and any additional rings can be independently aromatic, saturated or partially unsaturated, and can be fused, pendant, spirocyclic or a combination thereof "Hetero" means a group or compound including at least one heteroatom (e.g., 1-4 heteroatoms) each independently N, O, S, Si, or P.

A "hydrocarbon group" means a group having the specified number of carbon atoms and the appropriate valence in view of the number of substitutions shown in the structure. Hydrocarbon groups contain at least carbon and hydrogen, and can optionally contain 1 or more (e.g., 1-8, or 1-6, or 1-3) heteroatoms selected from N, O, S, Si, P, or a combination comprising at least one of the foregoing. Hydrocarbon groups can be unsubstituted or substituted with one or more substituent groups up to the valence allowed by the hydrocarbyl group independently selected from a $C_{1-30}$ alkyl, $C_{2-30}$ alkenyl, $C_{2-30}$ alkynyl, $C_{6-30}$ aryl, $C_{7-30}$ arylalkyl, $C_{1-12}$ alkoxy, $C_{1-30}$ heteroalkyl, $C_{3-30}$ heteroarylalkyl, $C_{3-30}$ cycloalkyl, $C_{3-15}$ cycloalkenyl, $C_{6-30}$ cycloalkynyl, $C_{2-30}$ heterocycloalkyl, halide (F, Cl, Br, or I), hydroxy, nitro, cyano, amino, azido, amidino, hydrazino, hydrazono, carbonyl, carbamyl, thiol, carboxy ($C_{1-6}$alkyl) ester, carboxylic acid, carboxylic acid salt, sulfonic acid or a salt thereof, and phosphoric acid or a salt thereof. While stereochemistry of the various compounds is not explicitly shown, it is to be understood that this disclosure encompasses all isomers.

All cited patents, patent applications, and other references are incorporated by reference in their entirety.

While the invention has been described with reference to exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for the manufacture of a composition comprising a polyketal adduct I

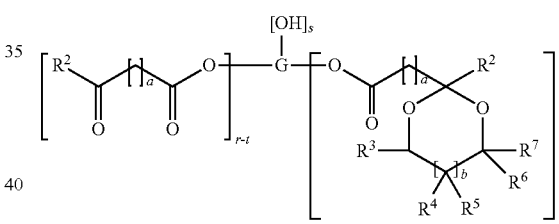

wherein

G is ethylene, 1,4-butylene, or 1,6-hexylene having a valence of g, wherein g=2, $R^2$ is methyl, $R^3$ is each independently hydrogen or $C_1$-$C_6$ alkyl, $R^4$ and $R^5$ are each independently hydrogen or $C_1$-$C_6$ alkyl, $R^6$ is each independently hydrogen or $C_1$-$C_6$ alkyl, or $R^3$ and $R^6$ together with their directly attached carbons form a fused cycloaliphatic or aromatic ring having a total of 5-6 carbon atoms or 4-5 carbon atoms and 1-2 oxygen atoms, $R^7$ is each independently hydrogen, $C_1$-$C_6$ alkyl, or $C_5$-$C_6$ cycloalkyl that is optionally substituted with an oxygen in the ring and further optionally substituted with 1-2—$OR^{10}$ wherein $R^{10}$ is $C_1$-$C_3$ alkyl, a is 2, b is each independently 0 or 1, the method comprising forming an ester between a hydrocarbon polyol II $$G\text{-}[OH]_g \qquad\qquad II$$

and a ketocarboxy compound III in the presence of an ester-forming catalyst,

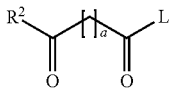

wherein
each ketocarboxy compound III is the same or different,
L is hydroxy, and
the forming an ester is conducted with at least 0.75 equivalents of the ketocarboxy compound III per one equivalent of hydroxy group in the hydrocarbon polyol II, to form a polyketocarboxylic ester IV

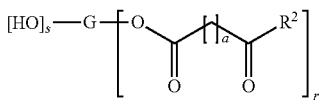

and
ketalizing polyketocarboxylic ester IV with a molar excess of polyol V relative to the Moles of polyketocarboxylic ester IV

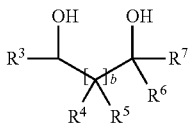

in the presence of a ketalization catalyst to provide the polyketal adduct I having less than 7 wt % of oligomers, wherein the oligomers are reaction byproducts that have a molecular weight higher than the molecular weight of the polyketal adduct I.

2. The method of claim 1, wherein the forming an ester is in the presence of sulfuric acid, arylsulfonic acid, hydrate of an aryl sulfonic acid, p-toluenesulfonic acid monohydrate, methane sulfonic acid, camphor sulfonic acid, dodecyl benzene sulfonic acid, perchloric acid, hydrobromic acid, or hydrochloric acid ester-forming catalyst, or a titanium tetraalkoxide, aluminum trialkoxide, tin II alkoxide, tin II carboxylate, organo-tin alkoxide, organo-tin carboxylate, levulinic acid, a tertiary amine, a quaternary ammonium hydroxide, a metal oxide, a metal hydroxide, or a combination thereof.

3. The method of claim 1, wherein the ester-forming catalyst is heterogeneous.

4. The method of claim 1, wherein the forming the ester between the hydrocarbon polyol II and the ketocarboxy compound III is conducted at a temperature of about 100 to about 260° C. and at a pressure of about 10 to 760 torr inclusive.

5. The method of claim 1, wherein the polyketocarboxylic ester IV is not isolated prior to the ketalizing.

6. The method of claim 1, wherein the polyketocarboxylic ester IV is isolated prior to ketalizing.

7. The method of claim 6, wherein the isolating is by washing or crystallizing to produce an isolated polyketocarboxylic ester IV.

8. The method of claim 7, wherein the isolated polyketocarboxylic ester IV is recrystallized prior to ketalizing.

9. The method of claim 1, wherein the ketalization catalyst is camphor sulfonic acid, dodecyl benzene sulfonic acid, sulfuric acid, hydrochloric acid, or a combination thereof.

10. The method of claim 1, wherein the ketalization catalyst is a heterogeneous acid catalyst.

11. The method of claim 2, wherein the ketalization catalyst is the same as the ester-forming catalyst.

12. The method of claim 1, wherein the ketalizing of the polyketocarboxylic ester IV with the polyol V is conducted at a temperature of about 60 to about 200° C. under a vacuum or under an inert gas purge.

13. The method of claim 1, further comprising distilling excess polyol V from the polyketal adduct I.

14. The method of claim 1, further comprising removing the ketalization catalyst from the polyketal adduct I comprising using a base, buffer, or anion exchange resin.

15. The method of claim 1, wherein the polyketal adduct I after ketalizing has a purity of greater than 50 wt % without further purification.

16. The method of claim 1, wherein polyketal adduct I comprises less than 1 wt % of an oligomer with a molecular weight greater than 500 Daltons.

17. The method of claim 1, wherein the polyketal adduct I has a yellowness index of less than 200 as measured by ASTM E313.

* * * * *